United States Patent [19]

Schulman

[11] 4,232,679
[45] Nov. 11, 1980

[54] PROGRAMMABLE HUMAN TISSUE STIMULATOR

[75] Inventor: Joseph H. Schulman, Los Angeles, Calif.

[73] Assignee: Pacesetter Systems, Inc., Sylmar, Calif.

[21] Appl. No.: 762,626

[22] Filed: Jan. 26, 1977

[51] Int. Cl.³ ............................................... A61N 1/36
[52] U.S. Cl. ............................................... 128/419 PG
[58] Field of Search ............... 128/2.1 A, 2 P, 2.05 R, 128/419 P, 419 D, 419 E, 419 PT, 421, 422, 423, 2.1 M, 631, 668, 670, 696–709, 731, 419 PG

[56] References Cited

U.S. PATENT DOCUMENTS

| | | | |
|---|---|---|---|
| 3,253,588 | 5/1966 | Vuilleumier et al. | 128/2.1 A |
| 3,667,477 | 6/1972 | Susset et al. | 128/419 E |
| 3,727,616 | 4/1973 | Lenzkes | 128/422 |
| 3,888,261 | 6/1975 | Maurer | 128/421 X |
| 3,898,984 | 8/1975 | Mandel et al. | 128/2.1 A |
| 4,019,518 | 4/1977 | Maurer et al. | 128/419 R |
| 4,024,875 | 5/1977 | Putzke | 128/423 R |
| 4,030,141 | 6/1977 | Graupe | 128/31.1 |
| 4,049,004 | 9/1977 | Walters | 128/419 PG |
| 4,066,086 | 1/1978 | Alferness et al. | 128/421 |

OTHER PUBLICATIONS

Deutsch, S., "A 15–Electrode Totally Implanted Time–Multiplex Telemetry Unit," IEEE Trans. on Comm., vol. COM-24, No. 10, pp. 1073–1078, Oct. 1976.
Waters, R. L. et al., "Experimental Correction of Footdrop by Electrical Stimulation of the Peroneal Nerve," Jrnl. of Bone & Jnt. Surgery, vol. 57-A, #8, Dec. 1975, pp. 1047–1054.
Gigauri, V. S. et al., "Instrmnt. for Autom. Monitoring of Muscle Relaxation of a Ptnt," Biomed. Engr., vol. 8, #4, Jul.-Aug. 1974, pp. 232–234.
Perritt, R. Q. et al., "A Simple, Inexpensive 8–Channel MUX for EMG in Human Locomotion," Med. & Biol. Engrg., Jan. 1976, pp. 104–106.

Primary Examiner—Robert W. Michell
Assistant Examiner—Francis J. Jaworski
Attorney, Agent, or Firm—Freilich, Hornbaker, Wasserman, Rosen & Fernandez

[57] ABSTRACT

An implanted heart and tissue stimulator is provided which is externally programmable so that stimulating signals generated thereby can be changed to meet the changing requirements of the user. Provision is made for verifying and screening control parameter words which are transmitted from an external controller so that only correct parameters will be stored for use by the implanted stimulator. Provision for read out of stimulating signals and of the tissue response thereto is also provided.

35 Claims, 25 Drawing Figures

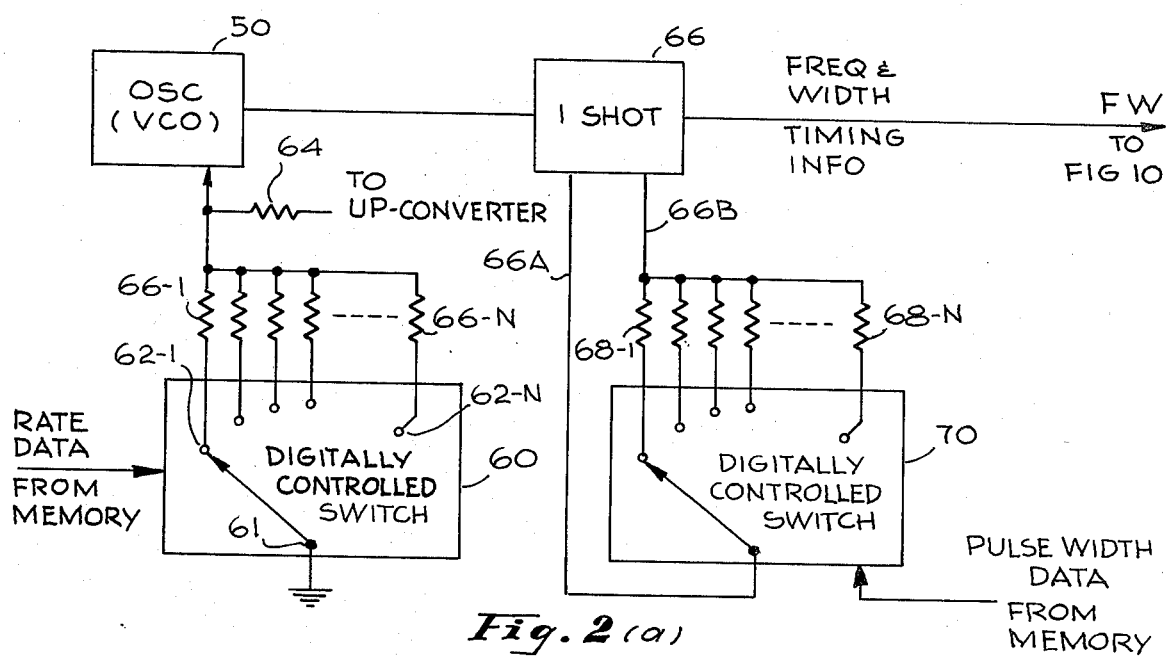
*Fig. 2(a)*
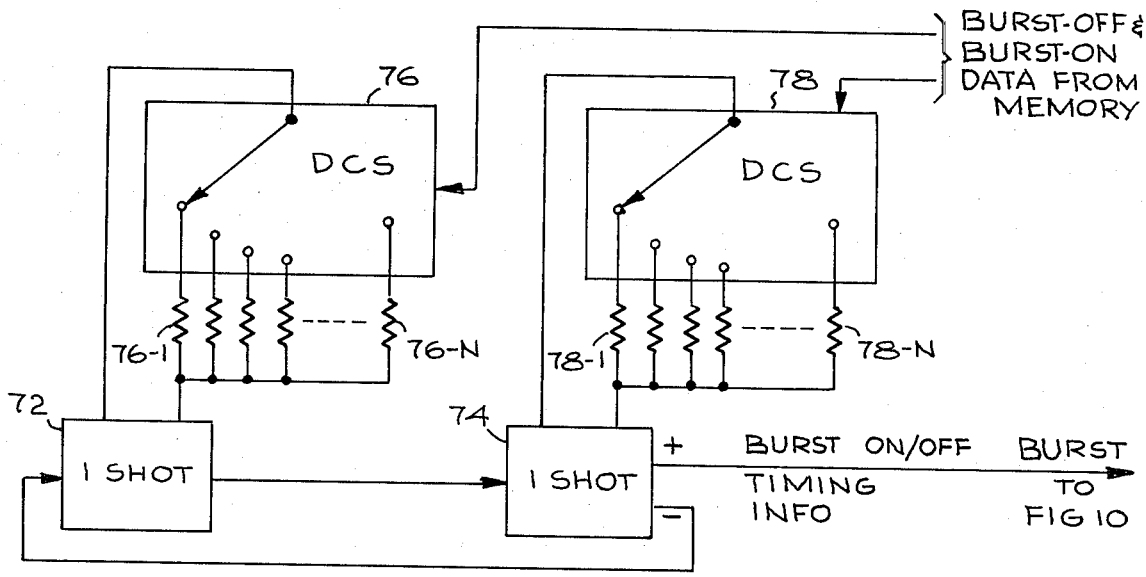
*Fig. 2(b)*
| IDENTIFICATION | | PARAMETER VALUE | PARAM TYPE | S T A R T |
|---|---|---|---|---|
| PATIENT NO. | HTS MODEL NO. | | | |
| 3 BITS | 3 BITS | 4 BITS | 3 BITS | 1 BIT |
*Fig. 3(a)*

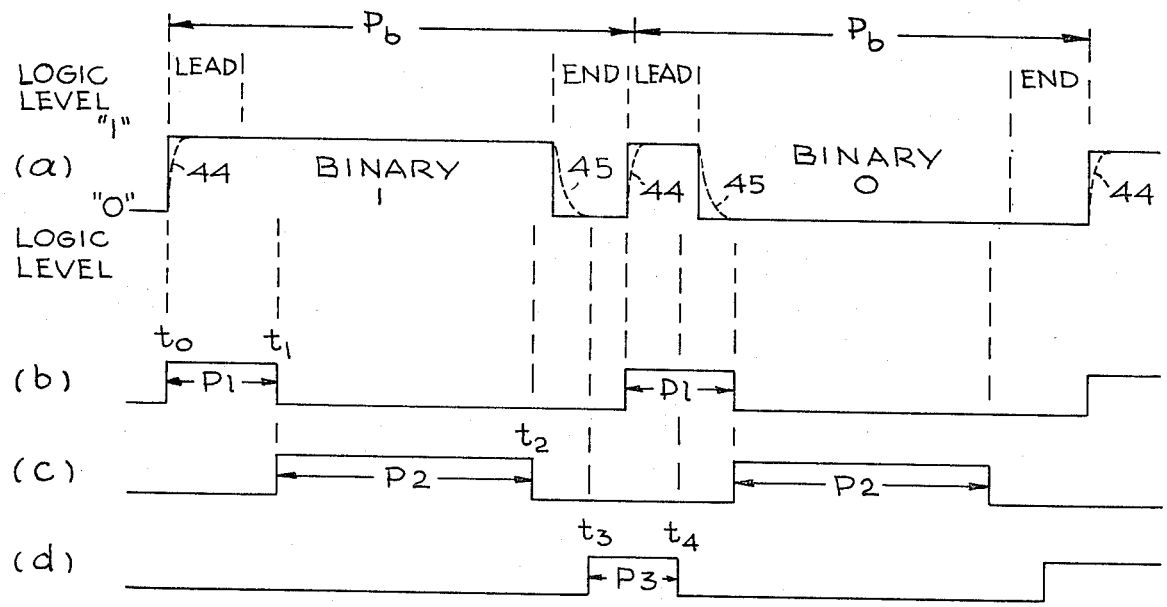
*Fig. 3(b)*
*Fig. 3(c)*
*Fig. 3(d)*
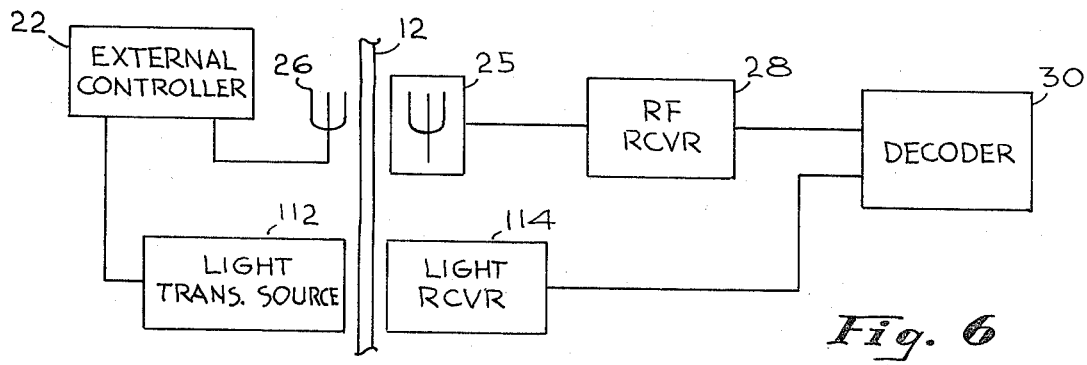
*Fig. 6*

| MODE PARAMETER VALUE | A | B | |
|---|---|---|---|
| 0 | OFF | OFF | |
| 1 | CONT | OFF | |
| 2 | OFF | CONT | |
| 3 | CONT | CONT | |
| 4 | BURST | OFF | |
| 5 | OFF | BURST | |
| 6 | CONT | BURST | |
| 7 | BURST | CONT | |
| 8 | BURST | BURST | PARALLEL (FIG. 8 LINES a & b) |
| 9 | BURST | BURST | ALTERNATE ( " " c & d ) |
| 10 | BURST | BURST | OVERLAP ( " " e & f ) |

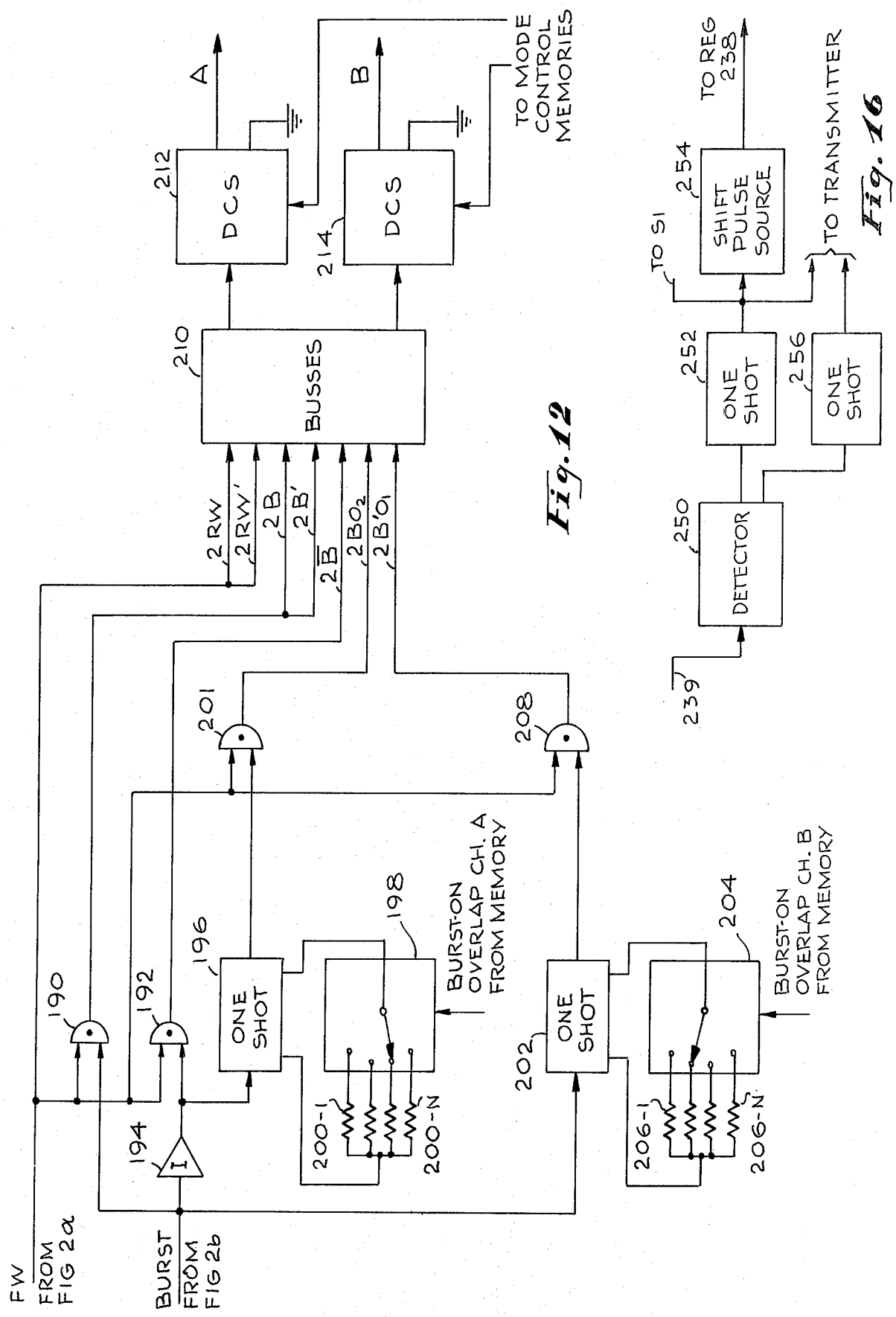

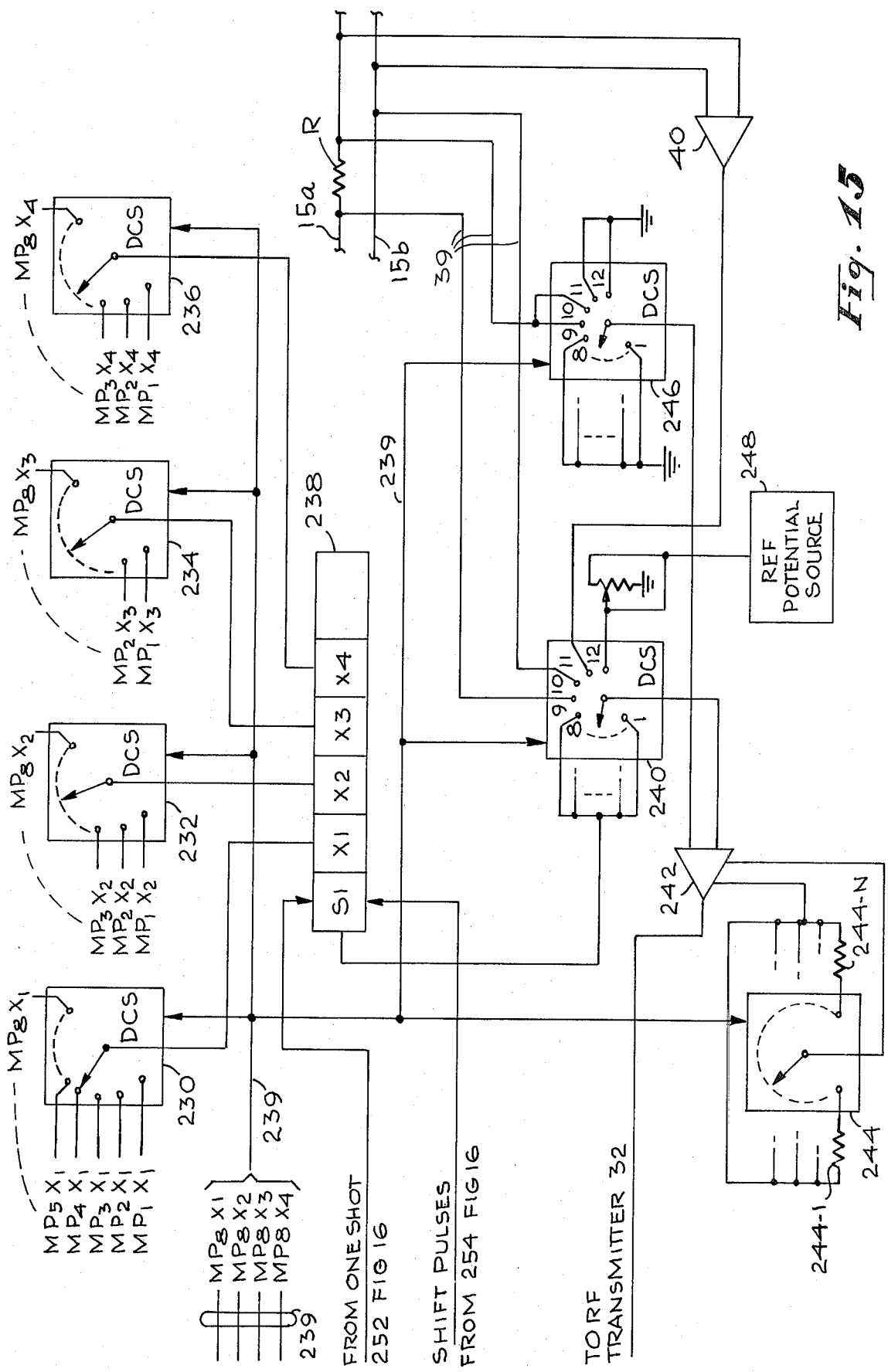

PROGRAMMABLE HUMAN TISSUE STIMULATOR

BACKGROUND OF THE INVENTION

1. Field of the Invention

The present invention generally relates to living tissue stimulators and, more particularly, to a programmable living tissue stimulator.

2. Description of the Prior Art

Various devices are presently in existence which are implantable in a human patient to stimulate body tissues. Among the best known of these devices is the cardiac pacemaker, which provides stimulating pulses to a patient's heart, via one or more electrodes, connected to the pacemaker through electrode leads. Many of the existing implantable cardiac pacemakers include a power source in the form of a battery, which is rechargeable by means of recharging power, transmitted to the implanted pacemaker from an external power source.

In recent years extensive research has been directed to develop stimulators for other than the heart, in order to relieve patients of the crippling effects of various physiological disorders. For example stimulators have been proposed to stimulate the brain, the spine, muscles, glands and organs or any other stimulatable matter. The stimulating pulses from these stimulators are intended to help patients, suffering from various disorders, e.g. cerebral palsy, spasticity, rigidity, epilepsy and other disorders, which are due to either improper, or the absence of natural stimulating pulses. Also, it has been appreciated that pain, such as phantom limb pain, resulting from a severed limb may be alleviated by applying stimulating pulses to the nerves proximal the damaged area. A workshop was held at the National Institute of Health, Bethesda, Maryland on Apr. 27–28, 1972, and a report of the workshop entitled "Functional Neuromuscular Stimulation" was published in 1972 by the National Academy of Sciences, Washington, D.C.

Different disorders require different stimulations. That is, the various parameters of the stimulating pulses, such as pulse amplitude, pulse frequency, pulse width, and other pulse parameters have to be different for different disorders and may differ from patient to patient. Furthermore, even for the same patient, the parameters may have to be varied depending on the patient's condition at any given time. Clearly, it would be prohibitively expensive to fabricate a customized stimulator for each patient. Furthermore, even if tailor-made for a specific patient, the stimulator would have to be capable of varying the pulses' parameters in order to vary the stimulation to suit the patient's changing conditions. Also, in a stimulator designed to stimulate tissue at different locations in the body, e.g., the right and left hemispheres of the brain, it is important to be able to control the relationships between the pulses to be applied to the different brain portions.

The only practical solution to the problem is to provide a basic implanted stimulator system, hereinafter referred to as a human tissue stimulator (HTS), which is programmable, in response to signals which are transmitted to the HTS from a source external to the body, in order to vary the parameters of the pulses which the HTS is to provide, to suit the needs of each particular patient depending on his type and state of disorder. Since the patient's safety is paramount, it is obvious, that the programmable HTS must be extremely reliable.

Also, it is very important to provide the programmer, e.g. a doctor, with an accurate indication of the parameters which were introduced into the HTS in order to verify that the proper parameters were accepted. Also in many cases it is desirable to observe the biological response to a stimulation by measuring the electrical potential produced by the tissues being stimulated.

Since we live in an environment which is noisy, i.e., one in which spurious electrical and other type signals, generally referred to as noise are present, it is extremely important that the signals which are transmitted to the implanted HTS to program it, in order to vary the parameters of the pulses provided thereby, are not affected or altered by the noise, and that, if affected the affected signals received by the HTS, do not cause improper pulse parameters, which, if permitted to be introduced and stored in the HTS may endanger the patient's life, particularly when stimulation takes place at such extremely sensitive parts of the body as the brain or the spine. Quite often a doctor after examining a patient may wish to change one or more of the parameters, e.g., pulse amplitude and not disturb the other parameters. Also, it is believed desirable to enable the patient himself to vary one or more selected parameters, if and when such variation is necessary, when the patient is away from the doctor's office. This capability may be desirable in order to alleviate unexpected discomfort or pain, as a result of the stimulating pulses and/or increase the stimulation when it is felt to be needed.

None of the known human tissue stimulators, which have been proposed to date, possess the desired capabilities as hereinbefore discussed. In the known stimulators, proposed to date, all parameters must be changed even when less than all of the parameters require change. Also, in most systems only the doctor can change the parameters, and even the doctor is not provided with a direct indication of the parameters introduced by him into the stimulator. Rather, the indication of the introduced parameters is provided indirectly, by recording or otherwise observing the response of the patient to the stimulating pulses, which are produced by the stimulator as a result of the doctor-introduced parameters. Furthermore, in the prior art during programming of the stimulator, the patient has to be practically in contact with the external programming unit, from which the programming signals are transmitted to the implanted stimulator, in order to minimize the effect of the ever-present noise. The patient cannot move about during programming and/or be at an appreciable distance, e.g., several feet, from the programming unit, which under some circumstances would be most desirable. For example, correcting a gait dysfunction by stimulating a nerve to a leg muscle to produce a normal walking motion.

OBJECTS AND SUMMARY OF THE INVENTION

It is a primary object of the present invention to provide a new improved programmable tissue stimulator.

Another object is to provide a programmable human tissue stimulator which is extremely reliable in that special means are included therein to practically insure that only the parameters chosen by a programmer to be stored in the stimulator are in fact stored therein.

Yet another object of the present invention is to provide a programmable human tissue stimulator in which one or more of the parameters stored therein, so as to control the characteristics of the stimulating pulses provided by the stimulator, may be varied without having to vary and change all the stored parameters.

These and other objects of the invention are achieved by providing an HTS which includes a plurality of memories in which are stored different parameters including all parameters necessary to control the characteristics of the stimulating pulses provided by the HTS. The HTS includes receiving and decoding circuitry, designed to receive digital signals in the form of multi-bit parameter words of unique formats and decode them. Special decoding criteria are employed to insure that only parameter words, which were not affected by noise, are permitted to vary the contents of any of the parameters in the memories. In the HTS of the present invention any one of the parameters, stored in any of the memories, may be changed without having to change or affect the parameters stored in the other memories. The contents of any one of the memories, as well as any one of several analog signals including biopotential signals may be transmitted out of the implanted HTS for verification purposes or other use. The HTS is operable to respond to doctor-programmed parameters, which are transmitted to the HTS from a master external programmer or from a patient-operated miniature control unit (MCU) with which the patient can affect the operation of the HTS and selected parameters stored therein.

The novel features of the invention are set forth with particularity in the appended claims. The invention will best be understood from the following description when read in conjunction with the accompanying drawings.

BRIEF DESCRIPTION OF THE DRAWINGS

FIG. 2a is a block schematic diagram exemplifying an oscillator which may be used with this invention.

FIG. 2b is a block schematic diagram of a pulse burst on/off timing generator.

FIG. 3a illustrates the contents of parameter words used by this invention.

FIG. 3b illustrates the contents of parameter words with redundancy.

FIG. 3c illustrates the contents of a parameter word which define the mode of its entry into a memory.

FIG. 3d is a drawing illustrating binary bit waveforms in accordance with this invention.

FIG. 6 is a block schematic diagram illustrating an alternative system for transmitting parameter words to the HTS.

FIG. 12 is a mode control circuit arrangement for applying pulses simultaneously to at least two tissues.

FIG. 15 is a block schematic diagram illustrating circuits which may be used for the selector, in accordance with this invention.

FIG. 6 is a block schematic diagram of a circuit for enabling the HTS transmitter to transmit the signals selected by the selector used with this invention.

DESCRIPTION OF THE PREFERRED EMBODIMENTS

Figure 1:
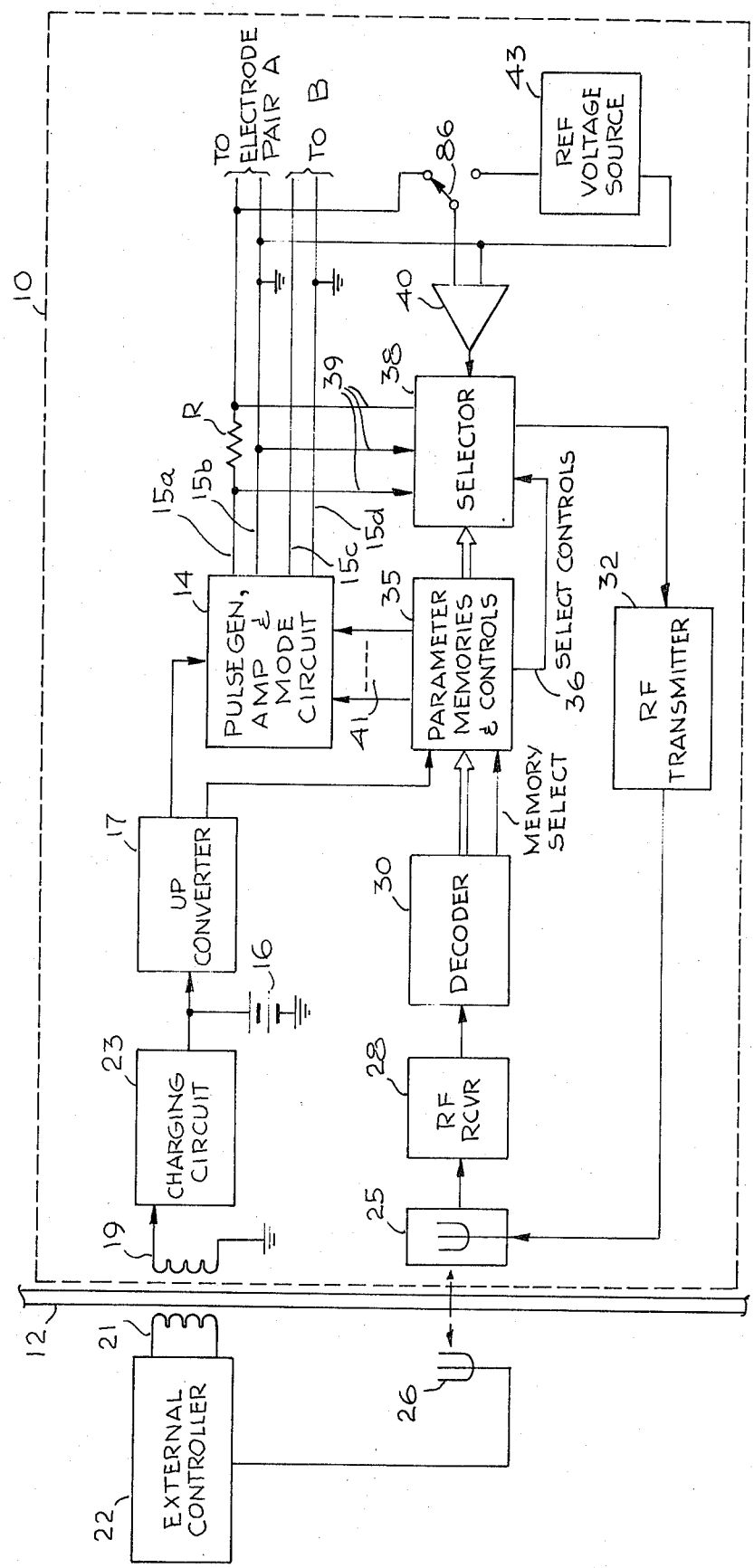
FIG. 1 is a block diagram of an embodiment of the invention.

Attention is now directed to FIG. 1 which is a simplified block diagram useful in explaining different significant aspects of the HTS of the present invention. However, as will become apparent from the following description, the invention is not intended to be limited thereto. In FIG. 1, numeral 10 designates a human tissue stimulator (HTS) which is assumed to be implanted below the skin 12 of a patient. The circuitry shown to the left of the skin 12 represents circuitry, external to the patient. The HTS includes some parts which are included in any conventional prior art HTS. However, the pulse generator, amplifier and mode circuit, 14, is not believed conventional and is hereinafter simply referred to as pulse generator 14, whose function is to provide stimulating pulses. These pulses by means of electrode leads 15a and 15b are assumed to be applied to electrode pair A, located at tissue A (not shown), e.g., a nerve or a muscle to be stimulated. The pulse generator 14 as well as other circuits in the HTS 10 are assumed to be powered from a power source, such as a battery 16, and if desired through an up-converter 17. The function of the latter, when used, is to raise the battery voltage in order to power those circuits requiring voltage higher or lower than that provided by the battery 16.

The particular HTS 10, shown in FIG. 1, the battery 16 is assumed to be of the rechargeable type, although other types of batteries may be used. The HTS includes means adapted to receive recharging energy from a source external to the body in order to recharge the battery 16. For explanatory purposes the recharging means inside the HTS is represented by a coil 19 which in inductively coupleable to an external coil 21 which forms part of an external controller 22. Charging energy from the external coil 21 is coupled into the implanted coil 19. The coupled energy from coil 19 is applied to a charging circuit 23 which is connected to the battery 16 to recharge the latter. Various arrangements are well known in the art for recharging an implanted battery and therefore the recharging circuitry will not be described in any detail.

In accordance with this invention the HTS 10 further includes an antenna 25, which for explanatory purposes is assumed to be a transmit and a receive (T/R) antenna for radio frequency (RF) signals. In the receive mode, signals e.g., RF signals from the external controller 22 are transmitted by an external transmitting antenna 26, are received by the implanted antenna 25 and are supplied to an RF receiver 28. The signals from receiver 28 are supplied to a decoder 30, whose function will later be discussed in detail. In the transmit mode implanted antenna 25 is used to transmit RF signals supplied thereto from an implanted RF transmitter 32 to the external antenna 26 which, in the receive mode, sends these signals to the external controller 22, for purposes to be discussed later.

Briefly, the information or data in the RF signals, received by the receiving antenna 25 from the external antenna 26, is in the form of multi-bit parameter words which include parameter values or simply parameters, which are to be stored in parameter memories, which form part of the implanted HTS. In order to insure that the received parameter words are not affected by noise and truly represent proper parameters the signals from the receiver 28 are decoded in the decoder 30. Only if the received parameter words are found to be proper and unaffected by noise are the parameter words, contained in them permitted to be transferred to and stored in the parameters memories, which together with their controls are represented by numeral 35.

As will be explained hereinafter in detail, one of the memories stores a read parameter, which is used to control, by means of select control lines, represented in FIG. 1 by single line 36, a selector 38. The latter, based on the read parameter which is supplied thereto determines which signals are supplied as input signals to the RF transmitter 32 for transmission, externally to the body. The selector 38 can be viewed as a multiposition switch. Assuming that the read parameter is 4 bits long, it can be used to control selector 38 to pass to transmitter 32 signals from any one of 16 different sources. In accordance with the present invention, these include the digital parameters in the various memories, as well as analog signals, such as the voltage of the stimulating pulses as represented across electrode leads, or the pulse current as measured across a resistor R, which are suppliable to selector 38 by leads 39. Also, as will be explained hereinafter the bipotential signal from the stimulated tissue A, present across leads 15a and 15b, may be amplified by an amplifier 40 and sent through selector 38 to the transmitter 32 for transmission external to the body. Also calibration signals to compensate instability in implanted components may be sent.

Basically, the parameters, stored in memories 35, except for the read parameter, are used to control the pulse generator and amplifier 14 in order to control their modes of operation as well as the characteristics of the train of pulses provided thereby, to the electrode leads 15a and 15b. These controls are supplied to pulse generator and amplifier 14 via control lines 41.

It should be noted that the HTS includes separate memories, designed to store the following parameters: frequency, amplitude, width, burst-on, burst-off, mode and read. The frequency and width parameters respectively control the frequency and width of the stimulating pulses, produced by the pulse generator, while the amplitude parameter is used to control the amplitude of the pulses. The mode parameter is designed to control the characteristics of the output pulse train to be either a continuous stream of pulses, referred to as a continuous mode, be in an off mode, in which no pulses are provided, or operate in a burst mode in which groups of pulses are provided to leads 15a and 15b, followed by periods during which no pulses are provided.

As will be explained hereinafter, in a multichannel embodiment in which pulses are suppliable through separate leads to electrodes at different tissues, the mode parameter may be used to control the mode of a train of pulses to the electrodes at the different tissues. The period during which the pulses are produced are defined by the burst-on parameters, while the period between groups of pulses is defined by the burst-off parameter.

For explanatory purposes, as hereinbefore assumed, each parameter is assumed to consist of 4 bits so that the parameter may assume any one of 16 different values. Thus, for the particular example, seven memories, each of 4 bits, are required. Each of these memories will hereinafter be referred to depending on the parameter stored therein, e.g., the frequency memory, the amplitude memory, etc.

Figure 2:
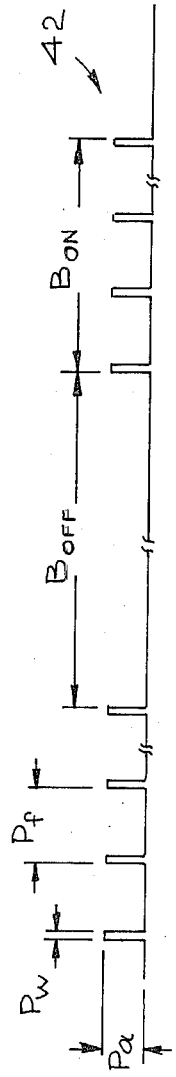
FIG. 2 is a pulse waveform diagram shown to assist in an understanding of this invention.
Figure 11:
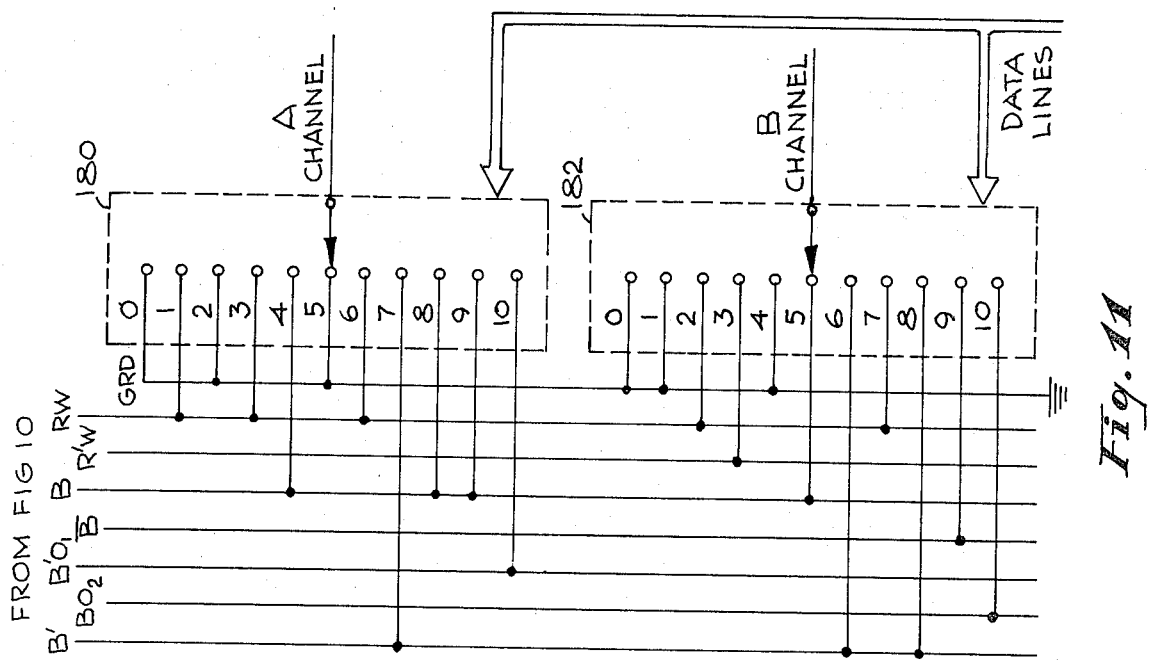
FIGS. 10 and 11 illustrate a mode control circuit arrangement for applying pulses alternately to at least two tissues.
Figure 10:
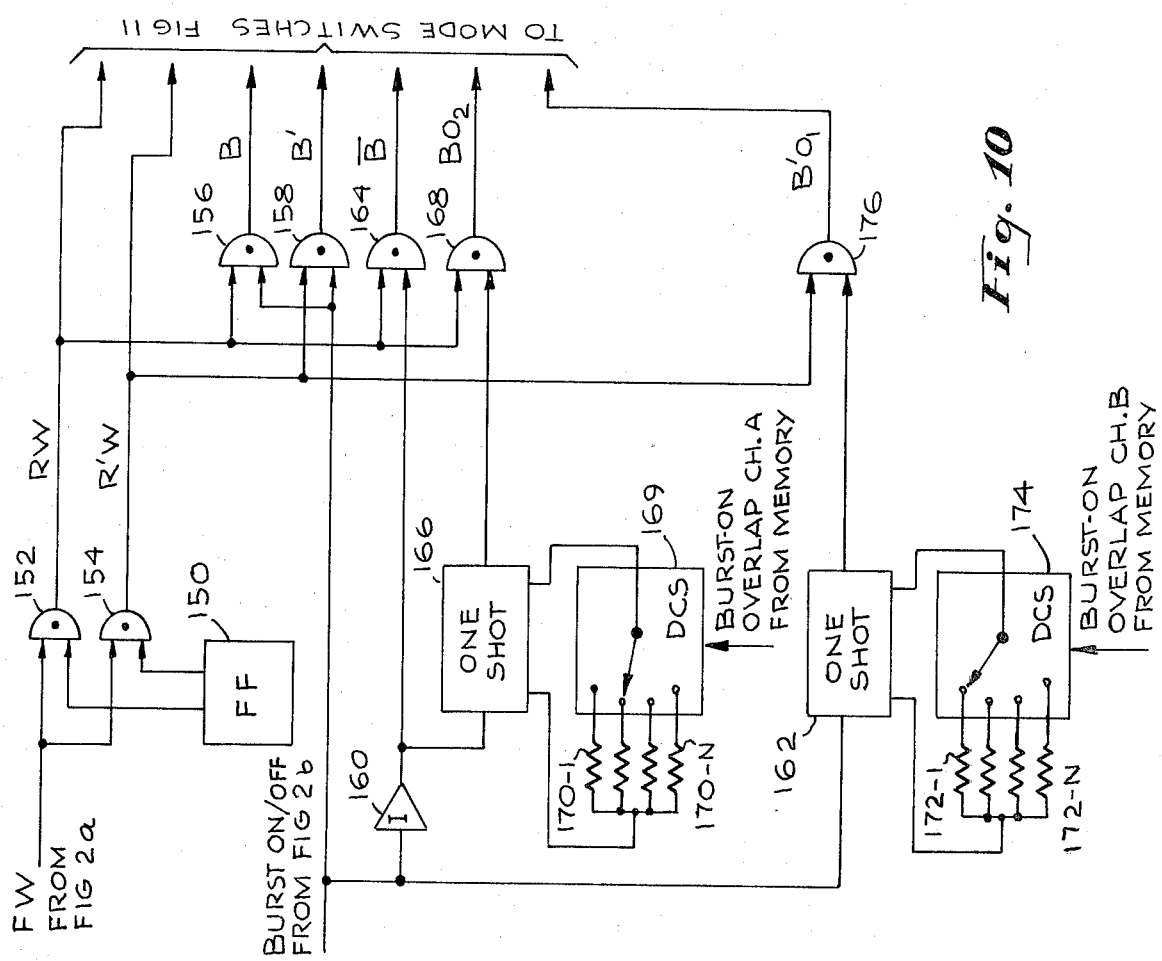
Figure 13:
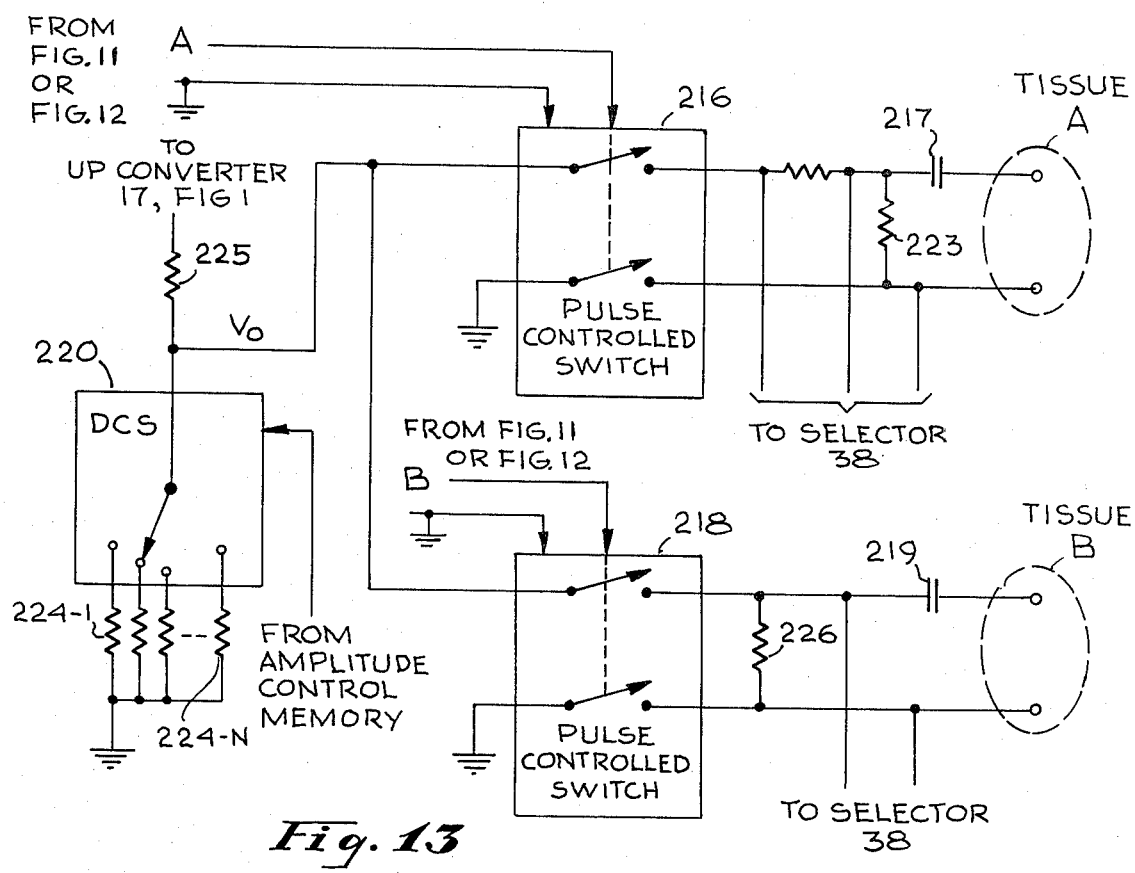
FIG. 13 is a schematic diagram illustrative of an amplitude control arrangement which may be used.

All the memories except the read memory, i.e., the one storing the read parameter, used to control selector 38, are connected to the pulse generator and amplifier 14 and its output stage by lines 41 to thereby control the pulses and their mode of delivery to the electrode leads. FIG. 2 is a simplified diagram of a train of pulses 42, shown in the burst mode. Pulse amplitude is designated by $p_a$, pulse width by $p_w$ and pulse frequency by $p_f$. The burst-on and burst-off periods, which are respectively controlled by the values of the parameters in the burst-on and burst-off memories are indicated by $B_{on}$ and $B_{off}$, respectively. Those familiar with the art will know that there are various known circuits which may be used to independently control the frequency, amplitude and width of pulses provided by a pulse generator and the output mode of the train of pulses. However, a preferred arrangement for a pulse generator is shown in FIG. 2a. FIG. 2b shows a schematic for burst off/burst on pulse control, FIGS. 10, 11 and 12 show mode control arrangements, and FIG. 13 is an amplitude control circuit. FIGS. 2a, 2b and 10 through 13 comprise the pulse generator, amplitude and mode circuits 14.

In FIG. 2a a voltage controlled oscillator (VCO), 50 has its frequency determined by the amplitude of a voltage which is applied thereto. The rate at which pulses are applied to tissue or nerve, by the HTS corresponds to the frequency output of the VCO. One of the parameters which the memory of the HTS stores is a digital word representing the desired pulse rate. This digital word is applied to a digitally controlled switch 60. The digitally controlled switch is an "off-the-shelf" component manufactured by Radio Corporation of America, and has a part number CD4067. It functions exactly in the manner of a selector switch connecting one common terminal to one of a plurality of other terminals in response to a digital data input. The common output terminal, 61, is connected to one of a plurality of terminals designated as 62-1 to 62-n. A voltage divider is established by connecting the up converter to one end of a common resistor 64. The other end of the common resistor is connected to the VCO and also to one of the ends of a plurality of resistors 66-1 to 66-n. The other end of each one of these plurality of resistors is connected to a different one of the terminals 62-1 to 62-n.

The way the circuit described operates is that a digital word from memory here, the "rate" determining word, is applied to the digitally controlled switch 60. This operates causing the digitally controlled switch to connect one of the resistors 66-1 to 66-n to ground. The one of the resistors to which connection is made is determined by the "rate" data word. The value of the resistor to which connection is made determines the voltage amplitude which is applied to the VCO and thereby determines the frequency of the VCO output or the pulse rate.

The output of the VCO is applied to a one shot circuit 66. The one shot circuit is driven in response to the VCO output and produces pulses at a rate determined by the VCO frequency. The on-time of the one shot circuit and therefore the width of the generated pulses is determined by the voltage across the one shot control terminals 66A and 66B. The width of these pulses is determined by inserting one of a plurality of resistors, respectively 68-1 to 68-n in the part of the one shot circuit which determines the width of its output pulse. This is done by using another digitally controlled switch 70, which, in response to a "Pulse Width" word from the memory, selects and connects one of the plurality of switches 68-1 through 68-n, into the width determining portion of the one shot circuit 66.

As will be described subsequently herein, one of the modes for the application of pulses by the HTS is a "burst" mode. FIG. 2b shows a burst on/off generator. It comprises two one shot circuits respectively 72, 74. The negative going trailing edge of one shot 72 drives one shot 74. The output of one shot 74 comprises burst on/off timing information. The negative going output of one shot 74 is used to drive one shot 72.

In similar fashion as was described in connection with one shot 66 and digitally controlled switch 70, the digitally controlled switch 76 is used to determine the pulse width of one shot 72 and digitally controlled switch 78 is used to control the pulse width one shot 74. The one of the resistors 76-1 through 76-n which is selected to be connected into the one shot 72 by the digitally controlled switch 76 is determined by the value of the digital "burst off" word from the memory. The value of the one of the resistors 78-1 through 78-n which is connected into the one shot 74 is determined by the value of the "burst on" word which is received from the memory.

Since one shot 74 must wait for the negative out put from one shot 72, the width of the output pulse of one shot 72 determines how long one shot 74 stays off. The width of the output pulse of one shot 74 determines how long a burst stays on. Thus, the output of one shot 74 provides burst on/off timing information.

As previously mentioned, in accordance with the present invention each parameter is transmitted to the HTS 10 by the external transmitting antenna 26, as a multi-bit parameter word. In accordance with the present invention, in one embodiment, each parameter word, in addition to the 4 bits, which define the parameter value, also includes several other groups of bits. These groups include a group of bits which are used to identify which parameter the word represents, i.e., parameter type bits, a start bit, which indicates the beginning of a parameter word, as well as a group of bits, used for other identification purposes. The latter may be used to identify the type or model of the HTS and/or a particular code, e.g., a number associated with the particular patient. Such identification bits, when included in each parameter word, are particularly useful to prevent a doctor, who may not be familiar with the HTS which is implanted in a patient, from varying the parameters in the HTS in a way which may be unsatisfactory or dangerous to the particular patient.

One example of the format of a parameter word is shown in FIG. 3a. Basically, therein the first bit (on the right hand side) represents the start bit. The next few bits, e.g., the 3 bits, identify the type of parameter which the word represents. Alternately stated, these 3 bits are used to identify a register (assuming the memory comprises a plurality of registers) into which the following 4 parameter value bits are to be stored. With 3 such bits up to 8 different registers or memories (parameter types), may be identified. The 4 bits which define the parameter value are followed by a plurality, e.g., 6 identification bits. For explanatory purposes these are assumed to include 3 HTS model identification bits, and 3 patient-number bits. Thus, in the particular example each word consists of $1+3+4+6=14$ bits.

Attention is now directed to line a of FIG. 3d in which two bits, one representing a binary 1 and another a binary 0 are diagrammed. The period of each bit is represented by $p_b$. In accordance with the present invention, whether a bit is a one or a zero, during each bit period the signal is high or a logic level "1", during a selected portion of the period $p_b$, e.g., the first 4 ms, hereinafter referred to as the lead portion, and is low or at a logic level "o" during a selected end portion of the bit period, which of explanatory purposes is also assumed to be 4 ms. The level of the signal between the lead and end portions of each bit period is high or a logic level "1", when the bit is intended to represent a binary 1 bit and is low or a logic level "0" whenever the bit is intended to represent a 0 binary bit. In FIG. 3d line a, the period during which the signal level is either a logic level "1" or "0" for each bit is assumed to be 17 ms for a total bit period $p_b$ of $4+17+4=25$ ms. This represents a bit rate of 40 bits/second. With a word format of 14 bits per word, the 7 parameter words may be transmitted to change the parameters in all seven memories in $14 \times 7/40 = 2.45$ second. With lead and end portions of 4 ms, the bits may be transmitted through telephone lines, where a minimum of approximately 3 ms is required for proper communication.

In FIG. 3d, line a, the changes in the signal level between the logic "0" and "1" levels are shown as abrupt by the solid lines. However, in practice, the changes are more gradual as indicated by dashed lines 44 and 45, which represent signal rise-time and fall-off-time, respectively. Such a bit pattern has been found to be very advantageous in the decoding of the received parameter words to insure that they have not been affected by noise, and thereby greatly increase the reliability in programming the HTS, which is of paramount importance to prevent serious or fatal injuries to the patient.

In accordance with the present invention, before a word which is received from receiver 28 is used to affect any of the parameters in the memories it is decoded by decoder 30. The decoder performs several screening functions. First it insures that the pattern of each bit is correct. That is, it has a lead portion of a logic "1" level of proper duration and ends with an end portion of a logic "0" level of proper duration. Secondly, it verifies that the central portion of the bit which defines whether the bit is a "1" or a "0" stays constant without any change for the proper length of time. This is a most important screening since if noise is present it would most likely interfere with the constancy of the central bit portion. Thirdly, it checks that the next bits start on time. Fourthly, it verifies that each word starts with a single 1 bit and ends with the proper number and types of the identification bits. For example, if the model identification bits are 010 and the patient number is 110, which for explanatory purposes may be prestored or preset in the decoder prior to implementing the HTS, the decoder verifies that each received word ends with six bits of 110010. It should be stressed that not all of these screens need be used. For example, only one or two screens may be used if it is felt that they would offer sufficient protection to the patient. Under very low noise conditions it is possible that no screens may be considered adequate.

If the pattern of any bit in a word is improper, which may be due to the effect of noise on the transmitted signals representing the word, the entire word is rejected and is prevented from modifying the memory. Also, even if all the bit patterns are proper but either the start bit is not a 1 and/or one or more of the identification bits are incorrect, the entire word is rejected. Only when an entire word is received and decoded, and found to be proper, i.e., its bit patterns are proper and all the identification bits match the proper prestored bits, is the word regarded as valid. The 3 bits which identify the type of parameter word are used to route the following 4 bits, which represent the parameter value, and store the latter in the proper memory.

It should be stressed that in the present invention it is not necessary to transmit the parameter word for all the memories. Since each word contains its own start indication, in the form of the start 1 bit, and other identification bits, any one parameter word may be transmitted to vary only one particular parameter in one of the memories. Since one of the memories is a read memory which stores the read parameter, which controls which parameter or analog signal which is to be supplied to the transmitter 32, any one of these may be chosen for transmission to the external controller 22. Clearly, with a read parameter in the read memory of 4 bits any one of 16 different signals may be supplied by selector 38 to the transmitter 32.

The external controller 22 may be designed so that as each parameter (other than a read parameter) word is transmitted to the HTS it is followed by a read parameter to cause the parameter in the previously transmitted parameter word to be transmitted back to the controller for verification. For example, after sending a frequency parameter word with a particular frequency parameter value, which is chosen by the doctor, the controller may send a read parameter word to read out the content of the frequency memory and supply its content to transmitter 32. Thus, the doctor may easily verify that the proper frequency value was stored in the HTS.

The controller may include a display by which the received parameter value may be displayed. Thus, if the transmitted frequency parameter was not affected by noise and was stored properly in the frequency memory it will be indicated by observing the display. If, however, the frequency parameter word was affected by noise or is otherwise improper, the transmitted frequency parameter is not permitted to be loaded in the frequency memory. Thus, if the frequency parameter which is displayed in the external controller differs from that which the doctor transmitted, this indicates to the doctor that the transmitted frequency parameter that he desired to store was not stored in the frequency memory as desired. Consequently, the doctor can then send a second frequency parameter word until its proper frequency parameter is stored in the frequency memory.

The controller 22 may also include means to enable the doctor to send any desired read parameter to choose the signals which are to be transmitted thereto by transmitter 32.

Attention is now directed to lines b-d in FIG. 3$d$ which will be used to describe the operation of the decoder in testing each bit pattern. As seen from line a, each bit starts with a "0"-"1" logic level transition and only one such transition is present, irrespective of whether the bit is a 1 or a 0. In the decoder this 0-1 transition is sensed at time $t_0$, (line b) and is used to activate time-period-defining circuitry, such as a one shot. The circuitry measures a first period P1 (line b) assumed to the 6 ms to inclue a lead portion of 4 ms. Basically, P1 is chosen so that it is long enough to insure that the signal level returns to "0" logic level if the bit is a 0 bit. Period P1 is assumed to end at $t_1$. From time $t_1$, a second period P2 (line c) is measured, where $P2 = t_2 - t_1$. P2 is chosen to be slightly less than the total binary level period, i.e., the bit period portion when the signal logic level is either a "1" or a "0" depending on the bit value. With this period, assumed to be 17 ms, since P1 is 6 ms so that it extends from about 2 ms into the binary level period, P2 is chosen to be $17 - 2 - 1 = 14$ ms long, so that it ends about 1 ms before the end of the binary level period position. During P2 the signal level is not supposed to change. If the bit is a "1" the logic level should be a "1", and should be "0" if the bit is a 0. If, however, due to noise the level changes during P2, the bit is deemed to be improper and the entire word is discarded.

It should be appreciated that $t_2$ occurs before the start of the bit end portion, which is assumed to be 4 ms long. A third portion P3 is measured starting after $t_2$, e.g., at $t_3$ when the end portion is expected to be stabilized at the "0" logic level. The period P3, lasting until $t_4$, is chosen so that it partially extends into the lead portion of the next bit when the logic level is "1". For the particular example, assuming that $t_3$ occurs at the middle of the end porton, i.e., 2 ms before the end of one bit, P3 may be chosen to be on the order of 4 ms to insure that it ends when the signal level stabilized at the logic "1" level, and before the end of the lead portion of the next bit. Since the end portion of one bit is at the "0" level and the lead portion of the next bit is at the "1" logic level a "0" to "1" transition must occur during P3. If it does not, the word is regarded as having an improper bit timing and the entire word is discarded.

It should thus become apparent that in the present invention two tests are performed on each bit. One test is to insure that its level does not change during most of its binary level period, as measured during P2. The other test is to insure that it ends with a proper end portion (a "0" logic level) and that the next bit starts with a proper lead portion (i.e. a "1" logic level). Such a double screening test practically insures that bits which may have been affected by noise are detected. This permits words which carry bits affected by noise to be detected and discarded.

Figure 4:
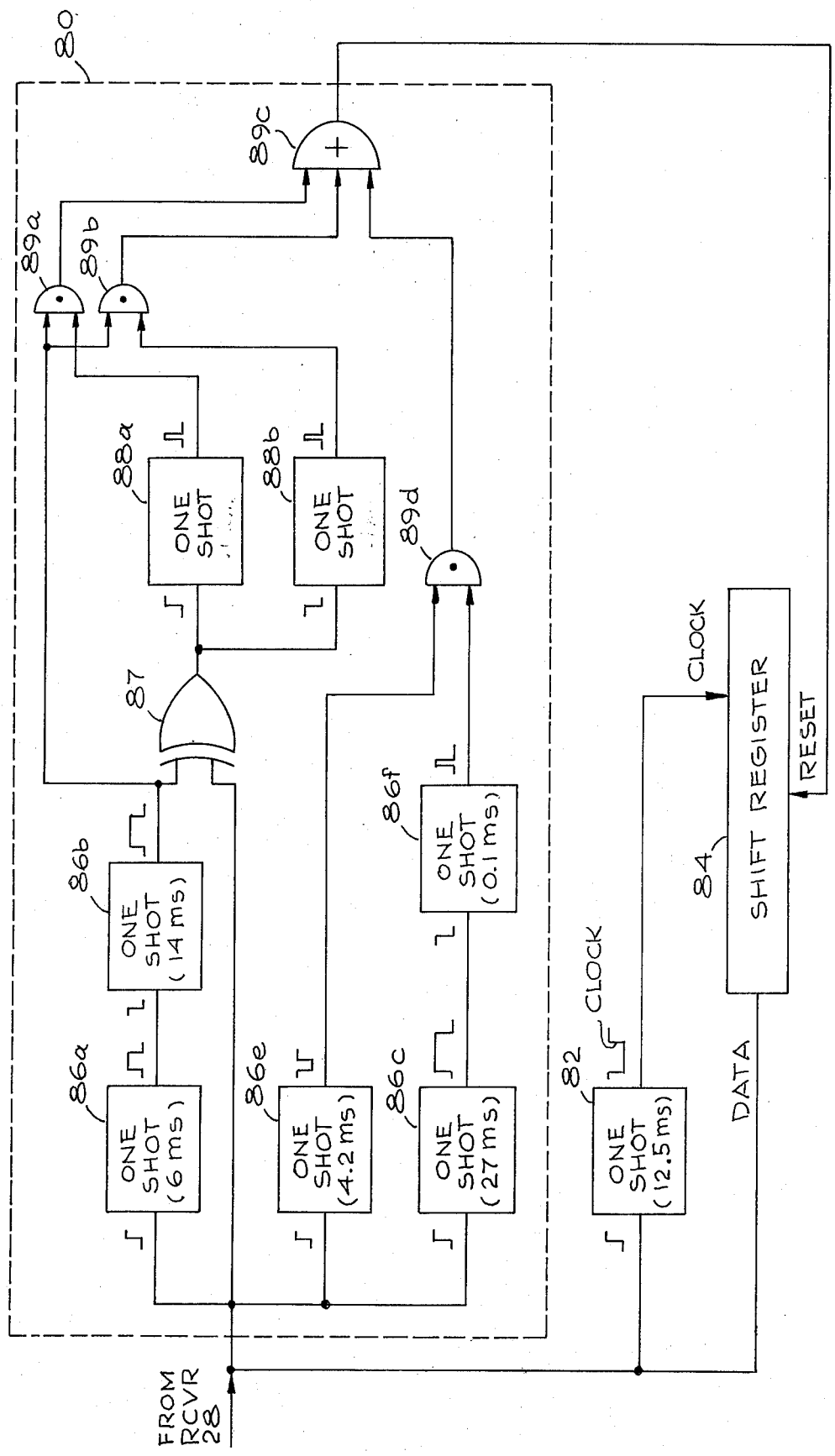
FIG. 4 is a block schematic of part of a decoder which is used in this invention.

Attention is now directed to FIG. 4 which is a partial block schematic of the decoder 30. Therein numeral 80 represents a bit pattern and screening circuit to which the bits from receiver 28 are supplied. The bits from receiver 28 are also applied to a one shot 82 which is activated by the "0"-"1" (low to high) logic level transition at the start of each bit. This one shot, in response, provides a clocking pulse at the mid point of each bit period Pb to a shift register 84. Thus if the bit is at a "1" logic level, a 1 is clocked into register 84, while a 0 is clocked therein if the bit received from receiver 28 is a 0. The bit pattern screening circuit 80 checks each bit pattern, as herebefore explained. If the bit pattern is proper, nothing happens. However, if the bit pattern is improper, the decoder 80 provides a reset signal to the shift register 84 to reset all the bits therein to a selected state, e.g., all zeroes, thereby discarding all the word bits, present therein.

Although different logic arrangements may be employed to implement the bit pattern screening circuit 80 a specific example is presented for explanatory purposes. The decoder 80 includes five one shots 86a, b, c, e, f, which provide output pulses of durations 6 ms, 14 ms, 27 ms, 0.1 ms, and 4.2 ms, respectively. The output pulses of 86a, b, c, and 86f are positive (high) and that of 86e is negative (low). One shots 86a, 86c and 86e, which are separately connected to the receiver output are triggered by 0-1 input transitions and one shots 86b, and 86f by 1-0 transitions, as diagrammed. Also included is an Exclusive Or-gate 87, whose output is supplied to one shots 88a and 88b which are respectively triggered by 0-1 and 1-0 transitions. The outputs of 88a and 88b are respectively anded with the output of one shot 86b by And gates 89a and 89b, whose outputs are fed to an Or gate 89c. The output of an And gate 89d is also applied to or gate 89c. The outputs of one shots 86e and 86f are applied to And gate 89d's inputs.

In operation, at the start of a bit, such as at time $t_0$ the 0-1 transition from receiver 28 triggers one shots 86a, 86c and 86e. The triggering of one shot 86e at this time is unimportant. At a time of 6 ms after $t_0$ one shot 86a triggers one shot 86b, which defines P2 which is 14 ms long by its high (1) output. If during P2, when the output of one shot 86b is high and if the bit is a 0 the output of exclusive Or gate 87 is a 1. If the bit level during P2 is not affected by noise, the output of exclusive Or gate 87 does not change and therefore neither of one shots 88a or 88b are triggered. Thus their outputs remain low and neither of gates 89a nor 89b is activated and therefore gate 89c is not activated, i.e., a reset pulse is not provided. If however during P2 the 0 bit undergoes a transition to a "1" logic level, due to noise, the output of gate 87 goes from 1 to 0, triggering one shot 88b which provides a short duration positive pulse, e.g., 0.1 ms, to And gate 89b. Thus, the latter is activated, turning on Or gate 89c which resets register 84. Similarly, if a bit is a "1" and during the 14 ms of P2 due to noise it drops to a "0" logic level, the output of gate 87 changes from 0 to 1, triggering one shot 88a which turns on gate 89a which in turn activates Or gate 89c to reset the register.

The one shot 86c defines the 27 ms period from the start of the bit. At the end of this period, i.e., time $t_4$, it triggers one shot 86f, which provides the very short duration (0.1 ms) positive pulse to And gate 89d. If less than 4.2 ms prior to $t_4$, a 0-1 takes place, as required, the one shot 86e is triggered and its output goes low. Consequently, when one shot 86f provides the 0.1 ms pulse the output of one shot 86e is low and therefore And gate 89d is not activated, and a reset signal is not produced by Or gate 89c. If however, due to noise, the start 0-1 transition of the next bit does not occur, or if a 0-1 transition occurs more than 4.2 ms prior to $t_4$ (i.e. less than 22.8 ms) one shot 86e is not triggered. Consequently, when one shot 86f provides its 0.1 ms positive pulse the output o 86e is high, and therefore And gate 89d is enabled, activating Or gate 89c to cause the register 84 to be reset. It should be pointed out that, when transmitting a string of bits, the last bit in the string, which ends with a 0 level end portion, has to be followed by a 0-1 transistion to enable the proper screening of the last bit.

Figure 5:
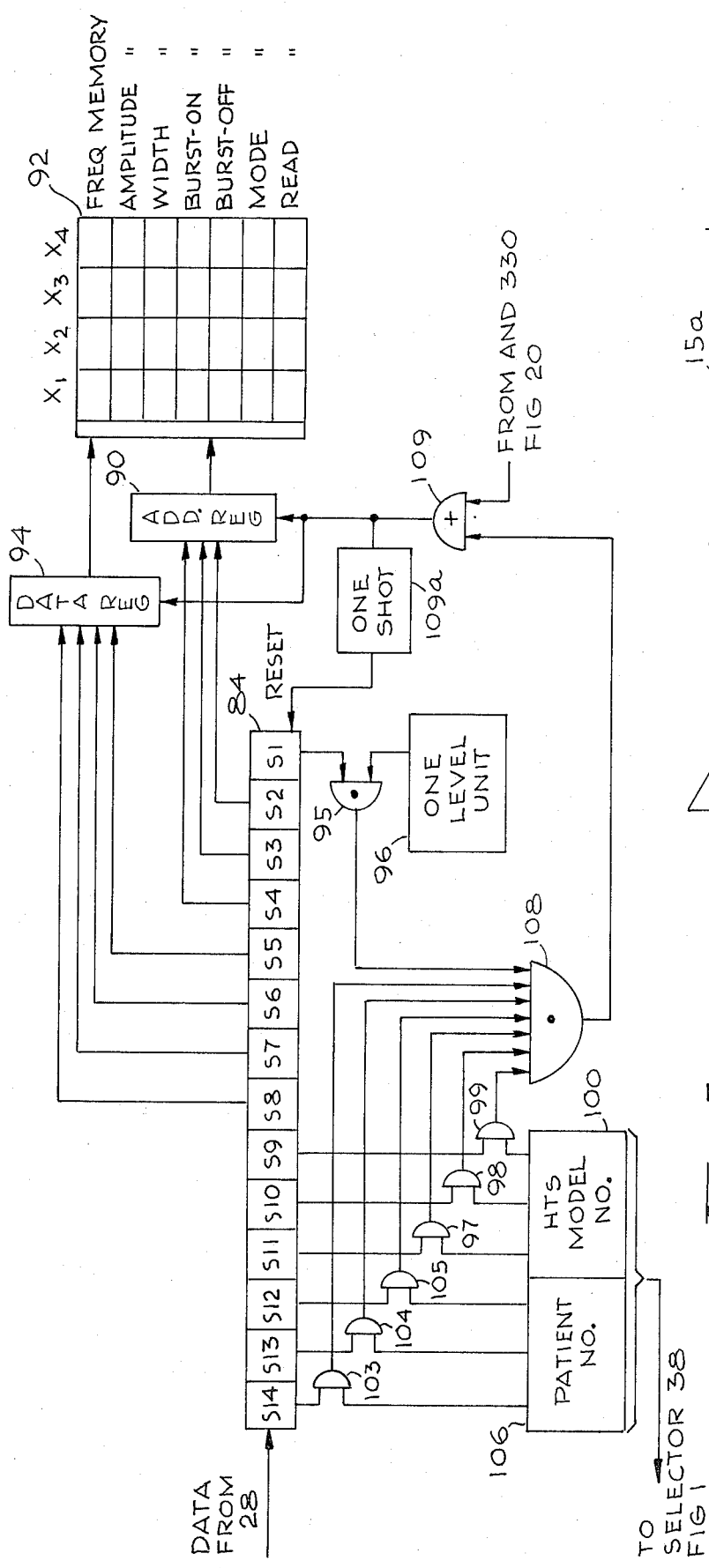
FIG. 5 completes the decoderblock schematic diagram and also illustrates the input to memory.

If the bits of a word have passed the pattern screening tests, shift register 84 will contain the bits of the word. Shift register 84 is also shown in FIG. 5, to which reference is now made. To simplify FIG. 5 the clock and reset lines to the shift register 84 are deleted. For a 14 bit word the shift register has 14 stages, designated S1-S14 from right to left, where S14 is the input stage and S1 is the last stage. Assuming that 14 successive bits have been found to have proper patterns, after each of them has been clocked into register 84, they are simultaneously present therein. If these 14 bits represent a complete parameter word the first bit in stage S1 should be a 1, since the start bit of each word is a 1 (see FIG. 3a). The next three bits in stage S2-S4 represent the parameter type or the memory into which the parameter represented by the bits in stages S5-S8 is to be stored.

As shown in FIG. 5 these stages (S2-S4) are connected to an address register 90 of a 4-bit ($X_1$-$X_4$) memory 92 representing a location in each address, memory 92 is that of a different memory (such as a set of flip flops). All of the memories are represented by block 35 in FIG. 1. The next 4 bits in stages S5-S8 represent the parameter itself. These stages are shown connected to a data register 94 of memory 92. The last 6 bits, S9-S14, are the identification bits. The 3 bits in stages S9-S11 are the HTS model number and the 3 bits in stages S12-S14 are the patient number.

In accordance with the present invention, before the parameter bits in stages S5-S8 can be stored in any of the addressed locations, in memory 92 the bits in S1 and S9-S14 are interrogated. The bit in S1 must be a 1. It is compared by a comparator 95 (represented by an And gate) with the 1 output of a one (1) level, unit 96. Only when the bit in S1 is a 1 does the output of 95 become high or a 1. Similarly, the bits in S9-S11 are compared by comparators 97-99 with the outputs of an HTS model number unit 100, in which the model number is assumed to have been prestored. Only when S9-S11 contain bits which represent the proper HTS model number are the outputs of all of comparators 97-99 high or 1's. Likewise, the outputs of all of comparators 103-105 are high when the bits in S12-S14 represent the proper patient number which is assumed to have been prestored in a patient number unit 106. The outputs of comparator 95, 97-99, and 103-105 are supplied to a 7-input And gate 108 which provides a high output only when all its inputs are high. The high output of gate 108 activates an Or gate 109 which produces a high output, representing a write signal. The write signal activates registers 90 and 94 to load the data, i.e., the 4-bit parameter value in register 94 into the memory at the address indicated in the register 90.

It should be appreciated that other arrangements may be used to load the 4 bits in S5-S8 into the address defined by the 3 bits in S2-S4. For example, S2-S4 may be viewed as the address register, and S5-S8 as the data register whose contents are used only when a write signal is produced. Thus, registers 90 and 94 are to be considered by way of example and not as a limitation on the invention.

Referring again to FIG. 5, a one shot 109a is also connected to the output of Or gate 109. When, Or gate 109 provides the write signal it also triggers one shot 109a, which, after a short delay period provides the reset signal to the shift register 84 to reset, all its stages to a zero state. The delay period, is chosen to be sufficiently long to insure that the data is transferred out of the shift register before it is reset. It is thus seen that the shift register is reset when the pattern of any bit in a word is improper or when an entire word is found to be proper.

From the foregoing it should thus be appreciated that in the HTS of the present invention, before a received parameter can be stored in its memory the multibit word containing the parameter is subjected to careful screening. The screening is used to insure that the word content is not affected by noise during transmission. The waveform of each of the word bits is separately screened. Only if the word bits are proper are they permitted to remain in register 84. Otherwise, the shift register is reset.

From the foregoing it may be seen that once screened bits are clocked into the shift register, the content of the register is screened to be sure that it contains a proper word. The word is screened to be sure that it has the proper start bit, such as the 1 start bit, and that it contains the proper identification bits. Only then, is the parameter included in the word, stored in its proper memory. With such a decoding technique the HTS is protected from being programmed by improper or noise affected parameters. This is very significant, since the life of a patient may depend on the HTS and its proper operation.

In the foregoing description it was assumed that the parameter words are received in the HTS only by the antenna 25 in the form of RF modulating signals, which are then supplied to the receiver 28 and therefrom to the decoder 30. If desired, the external controller, in addition to transmitting the parameter words as RF modulating signals, via the antenna 26, may also transmit them in other than an RF form. For example, it is well known that light penetrates the human skin. Therefore, light, modulated by the parameter words, may be used as a means to transmit the words into the implanted HTS.

An arrangement in which the parameter words may be transmitted via light is shown in FIG. 6. Therein, an external light transmitting source 112 is shown connected to the external controller 22 and is assumed to be modulated by the parameter words supplied therefrom. The HTS is shown to include an implanted light receiver 114 which responds to the modulated light from the external source 112 and generates electrical pulses in response thereto. The output of light receiver 114 is a stream of bits, representing the parameter words, originally provided by the external controller 22, unless they were affected by noise. The external controller may also, simultaneously with the transmission of light signals, transmit signals over the antenna 26, in the manner described.

The output of the light receiver 114 may be supplied to the decoder 30 and compared therein with the bits received from receiver 28. It should be apparent that since the parameter words are simultaneously transmitted by the external RF antenna 26 and the light source 112, the bits supplied to the decoder 30 by the two receivers 28 and 114 should be identical, unless one of them was affected by noise. Thus, in the decoder 30 the outputs of the two receivers 28 and 114 may be compared for identity. If indeed they are identical, thereby indicating that they are noise-free, the bits from one of the receivers are processed as hereinbefore described. If, however, the output bits from the two receivers are not identical, thereby indicating that one of them has been affected by noise, the bits are discarded and therefore prevent the word (or words) in which they are contained from affecting the parameters stored in the memories.

Since the parameter words are transmitted to the HTS by different means, such as RF signal and light, the likelihood that the same bit will be affected by noise in an identical manner is very small, if at all. Thus, by transmitting the parameter words by the two different carriers (such as RF and light) the accuracy of the received parameter words is greatly enhanced. In such an arrangement, if desired, the bit pattern may be simplified as well as the bit screening operations, as hereinbefore described. Although hereinbefore transmission of signals to the HTS by carrier such as RF signals and/or light has been described, it should be apparent that other techniques may be employed for such signal transmission. For example, magnetic induction, sound mechanical motion or conducted electric current may be used to transmit the signals to the implanted HTS.

It should be stressed that the purpose of screening a word to verify that it was not affected by noise is to increase the probability that the parameter value and parameter type are noise free, i.e., the same as those chosen by the doctor for transmission. Although it is important that the parameter value bits are noise free it is even more important to insure that the parameter type bits are noise free. Otherwise, a parameter value of one type, e.g., frequency, may be mistaken and stored in an improper memory, e.g., the amplitude memory.

In order to prevent this from occurring each parameter word may include redundant sets of bits which define the parameter type at different locations in the word. Then, in the decoder, these redundant sets of bits may be interrogated for identity. For example, for a redundancy of two sets per word, the last 3 bits (12th through 14th) of each word, instead of containing the patient number may contain 3 parameter type bits identical to those which follow the start bit. In the decoder the comparators 103-105, instead of comparing the bits in S12-S14 with the prestored patient number in 106 may compare them with the bits in S2-S4. Thus, a word will be accepted as valid only if the two sets of the parameter type bits are identical and the other identification bits are proper. Clearly each parameter word may be longer than 14 bits, e.g., 17 bits, to include both the previously described identification bits and the redundant parameter type bits. An example of the latter type word is diagrammed in FIG. 3b, in which a second set of parameter type bits is shown at the word end, following the patient number.

In the foregoing description it was assumed that stimulating pulses from the pulse generator 14 are supplied only to one pair of electrodes A to stimulate tissue located at one point in the patient's body. The invention is not intended to be limited thereto. There are a considerable number of applications in which tissues at different points in the body are to be stimulated. For example, tissues A and B at different locations in the brain may require stimulation to alleviate certain physiological defects. In accordance with the present invention the pulse generator and amplifier 14, may be controlled by the parameters in the memories and by the means of another pair of electrode leads, such as leads 15c and 15d, as shown in FIG. 1, may supply stimulating pulses to the electrodes at tissue B, which is at a different location than tissue A.

In practice, one can provide the HTS with a separate pulse generator and amplifier to provide stimulating pulses to each different tissue. In such an arrangement separate burst-on, burst-off and mode memories may be used for each one of the pulse generators. In order to reduce the size and cost of the HTS, it may be preferable to provide a single pulse generator and amplifier, such as pulse generator and amplifier 14 to stimulate the different tissues. In one embodiment actually reduced to practice, the single pulse generator and amplifier 14, are used to provide stimulation pulses to spaced apart tissues A and B and only the parameters in the three burst-on, burst-off and mode memories are used to control the characteristics of pulse trains to each of the tissues. In this embodiment the frequency, width and amplitude of the pulses, supplied to each of the tissues, are the same and are controlled by the parameters in the frequency, width and amplitude memories. Also, the burst-on and burst-off time of each pulse train is the same. However, the parameter values in the mode memory are used to control the properties or mode of the pulse train to each of the tissues.

Figures 7, 8:
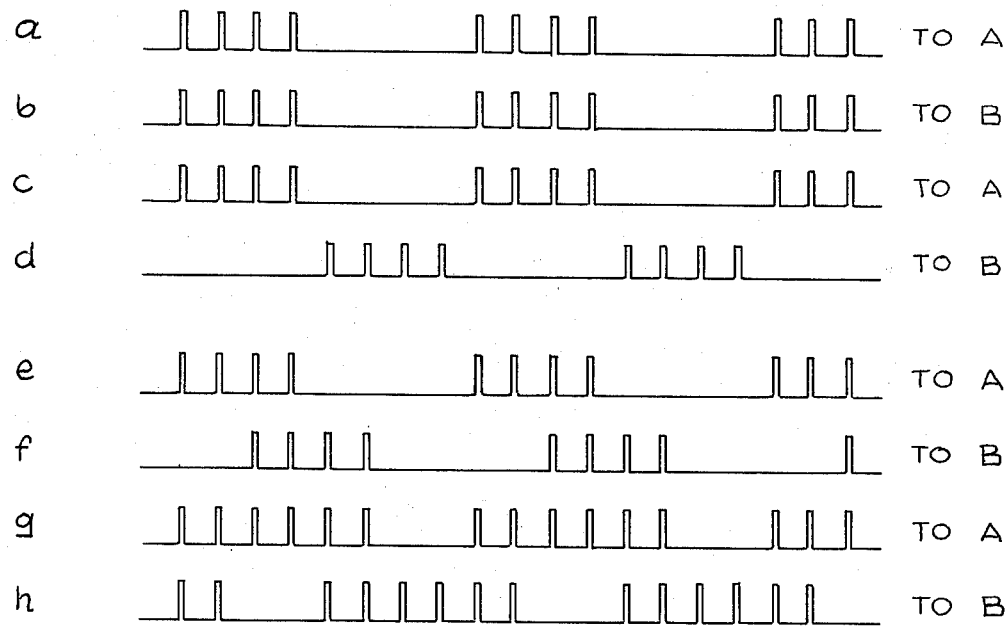
FIG. 7 is a table of pulse train modes used to stimulate two different tissues.
FIG. 8 is a waveform diagram illustrating modes of pulse wave trains applied to tissues.

FIG. 7 to which reference is now made is a table of the pulse train modes for tissues A and B, for different values of the mode parameters. It should be clear that the mode parameter value in the memory may control the output of the pulse generator so that the pulse train modes to A and B are both off, is continuous to A and is off to B, is off to A and is continuous to B, etc. Also, one of the pulse trains may be in a burst mode while the other is either off or continuous, as well as have both pulse trains in a burst mode. In the latter, the bursts of pulses may be supplied to the two tissues either in parallel, as represented in lines a and b of FIG. 8, alternately, as represented in lines c and d, or in an overlap pattern, as represented in lines e and f.

Therein, only partial overlapping is shown. If desired, complete overlapping may be achieved, as shown in lines g and h, by operating the system in the burst-burst overlap mode and by controlling the burst-on period to be more than 50% of the duty cycle.

Figure 9:
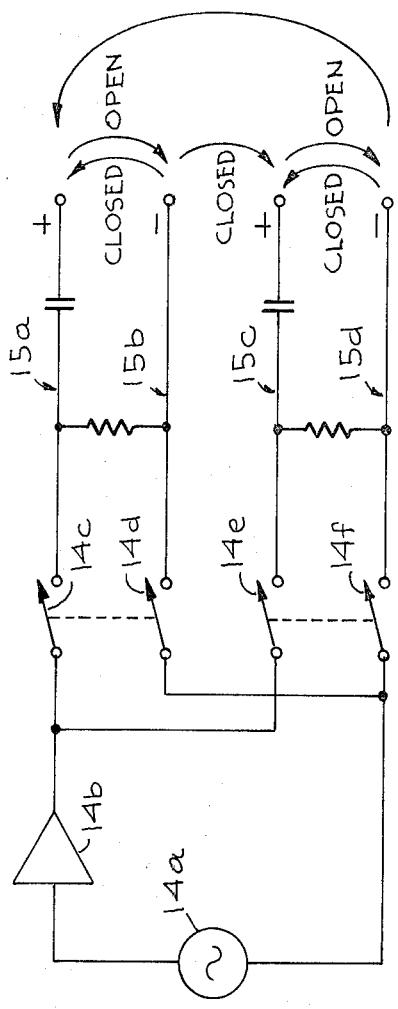
FIG. 9 illustrates schematically a single pulse generator connected for stimulating two tissues, shown to illustrate problems which may arise.

In FIG. 8 the pulses are diagrammed so that in the burst-burst parallel mode (lines a and b) and in the burst-burst parallel overlap modes (lines e and f, g and h) the pulses are shown to be applied simultaneously to the electrodes at both tissues A and B. This may be undesirable when the pulses are provided from a single pulse generator. The reasons may best be explained in connection with FIG. 9, wherein the single pulse generator is designated by 14a and its output is assumed to be amplified for example, by amplifier 14b, and switched to the outputs by switches 14c and d or switches 14e and f. If both channels are switched on simultaneously, not only will current flow from lines 15a to 15b and from lines 15c to 15d but current will also flow from line 15a to 15d and 15b to 15c. Between pulses the switches 14c, d, e and f are open. In that situation the capacitor in line 15a discharges through the resistor connecting 15a and 15b, thus current at the tissue terminals of 15a and b are flowing in a reverse direction, likewise with 15c and 15d. However, when the switches are open there is no current flowing between 15a and 15d, and between 15b and 15c. Thus, if one looks at the tissue, there will be an average d.c. current flow because the current flows during one part of the pulse in one direction and not during the off time of the pulse. This is very undesirable since excess current flow in one direction will cause either tissue destruction or excess tissue growth. To prevent this from occurring, without excessive isolation electronics, the novel plan that is used here is to have only one channel on at a time. Thus, the current flow between different channel pairs will never occur.

As may be seen in FIG. 10, frequency and width timing information, which is the output of one shot 66 in FIG. 2a, and which is designated as FW, is applied to a triggering flip flop 150, and to two And gates respectively 152, 154. The flip flop 150 is triggered between its two stable states and responds to every pulse it receives. The two flip flop outputs are used to enable the respective And gates 152 and 154 alternately, whereby the output from the two flip flops comprise alternate pulses, which are termed RW and RW'.

The burst on/off control signals from the circuit in FIG. 2b are applied, as one input, to two And gates respectively 156, 158. The other input to And gate 156 is the RW output of And gate 152. The other input to And gate 158 is the RW' output of And gate 154. The outputs from And gates 156 and 158 are respectively designated as B and B', and they are burst controlled alternate pulse outputs.

The burst on/off signals from FIG. 2b are also applied to an inverter 160 and to a one shot circuit 162. The output of the inverter 160 is applied to an And gate 164 whose other input is the RW output of And gate 152. And gate 164 output is designated as $\bar{B}$, and $\bar{B}$ pulses occur when B pulses do not occur.

The output of inverter 160 is also applied to a one shot circuit 166. One shot circuit 166 provides an output pulse whose duration is determined by a digitally controlled switch under control Channel A of burst on-overlap data from the burst on-overlap memory. In the manner described previously, in connection with FIG. 2a, the digitally controlled switch 169 will connect one of the resistors 170-1 through 170-n into the timing circuit of the one shot 166 whereby the width of the output pulse is determined. The output of the one shot circuit 166 is applied to an And gate 168, whose other input is the RW output of And gate 152. The output of this And gate 168 is designated as BO$_2$.

The burst on/off pulses from FIG. 2b are also applied to one shot 162, which provides, in response thereto, output pulses whose widths are determined in accordance with the one of the resistors 172-1-172-n which is selected by a digitally controlled switch 174, in response to digital word received from the memories to determine the Channel B "burst on-overlap". The output of the one shot 162 is applied to an And gate 176 whose other input is the RW' output of And gate 154. Signals B'O, and BO$_2$ determine overlap pulse trains on the respective A and B channels. All of the And gate outputs 156, 158, 164, 168 and 176 are connected to buses and then to 10 position digitally controlled switches, which can be called mode switches.

FIG. 11 shows the arrangement for connecting the signals generated by the circuitry shown in FIG. 10 to busses and then to the 10th position digitally controlled mode switches. Two mode switches respectively 180 and 182 are employed. These are of the type described previously which, in response to the mode parameter words from the memories connect one of ten inputs to a signal output. Mode switch 180 signal output is the A channel output. Mode switch 182 output is the B channel output. The buses are designated with the same labels as are shown in FIG. 10. There is a B' bus which connects to terminal 7 in switch 180 and terminal 8 in switch 182. A BO₂ bus connects to contact 10 in switch 182. A B'O₁ bus connects to the contact 10 in switch 180. A B bus connects to contact 9 in switch 182. A B bus to contacts 4, 8, and 9 in switch 180 and contact 5 in switch 182. An RW bus which connects the contacts 1,3 and 6 in switch 180 and to contact 2 and 7 in switch 182. A ground bus connects to contact 0,2 and 5 in switch 180 and to contact 0, 1 and 4 in switch 182.

It can be seen that by selectively activating two mode switches 180 and 182 anyone of the combinations shown in FIG. 7 with pulses positioned alternately may be selected. FIG. 12 is a circuit arrangement for producing superimposed pulse trains which may be thereafter combined using a bus and mode switch arrangement such as is shown in FIG. 11 for obtaining pulse train arrangements on the A and B channel with pulses being simultaneously on both channels.

In FIG. 12, the FW output from the circuits of FIG. 2a is at twice the frequency of the RW and RW' pulses shown in FIG. 10 and are designated on the output lines as 2RW and 2RW'. The FW output is applied to an And gate 190. A second input to And gate 190 consists of the burst on/off pulses from the circuits shown in FIG. 2b. The output of And gate 190 is designated as 2B and 2B'. The reason for the designation of the number 2 is because these pulses occur at twice the frequency of the FW or B or FW' or B' pulses. The prime designations are adopted in order to simplify bus connections, although unlike the situation in FIG. 10, the 2 FW' and 2B' pulses do not occur alternately with the respective 2FW and 2B pulses but are the same.

The FW pulses train is also applied to an And gate 192, whose other input is received from an inverter 194. The inverter input comprises the burst on-off pulses from FIG. 2b. The output of And gate 192 is designated as 2B. The inverter output is also applied to a one shot circuit 196, whose pulse duration is determined by a digitally controlled switch 198. The switch 198 will insert, in the timing circuit of the one shot 196, the one of the resistors 200-1 to 200-n selected by the digitally controlled switch in response to a word from the burst on memory which is to control the timing and duration of the pulse bursts. The output of the one shot 196 is applied to an And gate 201, whose other input comprises the FW pulse train from FIG. 2a. The output of the And gate 201 is designated as 2BO₂.

The burst on/off control pulsetrain is applied to another one shot circuit 202, which is controlled by a digitally controlled switch 204. The digitally controlled switch, in response to a word from the burst on memory for the B channel, selects for insertion into the timing circuit of the one shot 202, one of the resistors 206-1 to 206-n, whereby the pulse width of the output of the one shot 202 is controlled. One shot 202 output is applied to an And gate 208, whose other input comprises the FW pulses. The output of And gate 208 is designated as 2B'O₁.

All of the outputs of FIG. 12, the numeral 2 in front of RW and RW' B, B', B, B'O₂ and B'O₁, are designated essentially the same as the outputs obtained from FIG. 10. Accordingly, an arrangement for connections to and from the buses, here represented schematically by a rectangle 210, labelled buses, will be the same as is shown in FIG. 11, and the connections to the two digital control buses, 212, and 214, of the buses 210 will be the same as is shown in FIG. 11. The digital control switches 212 and 214 are controlled in response to digital word signals from the mode control memories to provide pulse trains outputs in which the pulse trains are in parallel, and may be in any one of the 10 modes represented by a chart shown in FIG. 7.

FIG. 13 is a schematic diagram illustrating an amplitude control system that may be used. The output pulses from digitally controlled mode switches 180 and 182 in FIG. 11 or from the digitally controlled mode switches 212 and 214 in FIG. 12 are connected to the respective double pole double throw pulse control switches respectively 216, 218. The input to both of these pulse control switches is received from a variable voltage divider network. This network comprises a digitally controlled switch 220, which, in response to a digital word signal from the amplitude control memory connects a resistor 222, in series with a selected one of resistors 224-1 to 224-n. The voltage divider network is connected across the output of the up converter 17, shown in FIG. 1. Accordingly, a voltage $V_0$ is derived for the junction between the resistors 222 and the one of the resistors 224-1 to 224-n. This voltage is applied to the tissue A, or tissue B, or both, whenever the pulse controlled switches 216 and 218 are actuated in response to the pulses applied to them from the mode control switches. Capacitor 217, in series with the output lead 15A, in conjunction with the capacitor discharge resistor 223 provides equal coulombic flow in both directions at the stimulating electrodes. Equal coulombic flow is required to prevent tissue damage which can occur when an average DC current flows through the tissue. Capacitor 219 and resistor 226 serve the same purpose in channel B. It should also be pointed out that resistor 223 could be replaced with a switch that is open when switch 216 is closed, and closed when switch 216 is open (i.e., is out of phase with switch 216). A similar switch out of phase with switch 218 could replace resistor 226. This will permit a rapid discharge of the output capacitor 217 in A and 219 in B immediately upon completion of an output pulse. It is felt in the medical community that such a rapid discharge is more desirable to protect the tissue from the danger of D.C. current flow.

Attention is once again directed to FIG. 1 for the purpose of describing other aspects of the invention. The pulse generator, amplitude and mode circuit is shown connected to leads 15a and 15b, thereby being effectively connected to electrodes A at tissue A. After tissue is excited, either spontaneously or by a stimulating pulse, from the HTS, a voltage (biopotential signal) is produced by the tissue which is actually sensed by the electrodes and is therefore present across leads 15a and 15b. Thus, the biopotential signal from tissue A after it has been stimulated is applied to amplifier 40. This biopotential signal is amplified by amplifier 40 and is supplied to the selector 38. As previously explained, the selector 38 is controlled via the select line 36, in response to a read parameter in the read memory, to select an input which is to be supplied to the RF transmitter 32 for transmission to the external controller 22.

Such a capability is most desirable since it enables the doctor to observe an accurate reproduction of the biopotential signal without its waveform having been deformed, which is the case when the biopotential ia sensed indirectly by means of external electrodes, e.g., the taking of an EKG by means of externally attached electrodes. The accurately reproduced biopotential signal may be used for diagnosis purposes as well as to determine the desired characteristics of the stimulating pulses to be applied to the tissue.

In order to prevent distortion of the received biopotential signal it may be desirable to be able to control the gain of the amplifier 40 so as to prevent signal clipping if the gain is too high. This may be achieved by including an additional memory which may be referred to as a gain memory, in which a gain parameter may be stored in order to control the gain of amplifier 40.

As shown in FIG. 1 the electrode leads 15a 15b are connected via leads 39 directly to the selector 38. Also leads 39 connect the selector across a resistor RW in series with lead 15a. The selector, when activated by a proper read parameter value, can apply the stimulating pulses which are sent to the electrodes A at tissue A, or the pulse current, to the transmitter 32 for transmission externally of the body. Thus, a doctor may observe not only the biopotential signal at tissue A but also the stimulating pulses when such pulses are applied to the electrodes A. It should however be appreciated that the stimulating pulses and the biopotential signal cannot be transmitted out nor observed, simultaneously. Another amplifier, similar to that of 40, may be used to amplify and send to the selector 38 the biopotential signal at tissue B, and the electrode leads 15c and 15d may be connected to the selector 38 to enable the stimulating pulses which may be sent to tissue B to be transmitted out of the HTS to the external controller. If desired both lead pairs, 15a, 15b and 15c, 15d may be connected through appropriate switches to amplifier 40, and the biopotential signals from either tissue A or tissue B may be selectively applied to amplifier 40 in response to an external proper command, which is transmitted to the HTS.

For example the HTS may include a flip flop whose state controls a lead by means of which power is connected to the amplifier. The state of the flip flop may be changed by transmitting a particular word, wherein when decoded, in the HTS controls the state of the flip flop.

In diagnosing the biopotential signal from either of the tissues, e.g., tissue A, it may be important to know the exact amplitude of the biopotential signal which the tissue A produces. Since the amplifier 40 may experience some drift, i.e., changes in gain, the capability of calibrating the amplifier 40, even though it is in the implanted inaccessible HTS may be desirable. This may easily be achieved by briefly applying a preselected calibrated input voltage, represented by v, which may be derived from battery 16, to the amplifier 40 during the absence of the biopotential signal from tissue A and transmit the amplifier output to the external controller 22. Based on the amplitude of the reference signal the doctor can calibrate and determine the exact amplitude of the biopotential signal when the latter is applied as the input to amplifier 40.

This potential v may be applied to the amplifier 40 through a switch 86 which may be commanded to switch from lead 15A to a reference voltage source 43. This switch command can be introduced either by an unused particular parameter value or by a separate calibration parameter which can be stored in a separate calibration memory. This is illustrated in FIG. 1. Clearly, the amplifier associated with amplifying the biopotential signal of tissue B may be similarly calibrated. In fact, if a separate calibration parameter is used one value may be used to calibrate the gain of amplifier 40 while another value may be used to calibrate the amplifier which is used to amplify the biopotential signal of tissue B. Also, if desired other values in the separate calibration memory may be used to apply different calibration signals such as linearity, frequency response or other characteristics to the amplifier (or amplifiers) which is (or are) used to amplify the biopotential signals from tissues A and B.

Hereinbefore it was assumed that the stimulating pulses are unipolar, as shown in FIG. 8, and that the same leads 15a and 15b on which the stimulating pulse is applied to the electrodes to stimulate the tissue, such as tissue A are also used to apply the biopotential signal to the amplifier 40. With such a unipolar stimulating pulse the pulse voltage discharge or decay time through the body solution at the tissue is reasonably long. This aspect may be explained in connection with FIG. 14 wherein, in line a there is represented the unipolar stimulating pulses 220a, and in line b there is represented the voltage decay waveforms 220b. The full decay time is relatively long, due to the effective electrode-tissue electrical capacitance. Since the biopotential signal represented in line b by 221 typically occurs close to the stimulating pulse, if the decay time is long the biopotential signal may occur before the stimulated voltage has fully decayed and may be overshadowed by its relatively larger amplitude.

To overcome this problem separate electrodes may be used to sense the biopotential signal and supply it through separate leads to the amplifier 40. However, to reduce the number of electrodes, which have to be inserted into the tissue and the number of leads, the problem may be overcome as follows.

Figure 14:
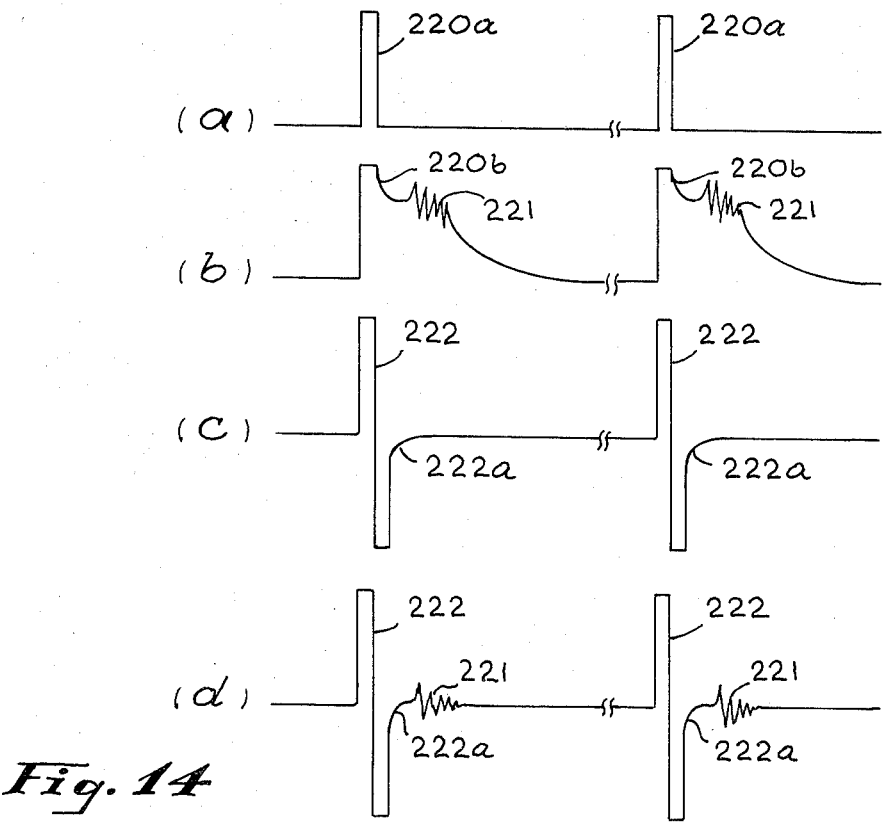
FIG. 14 is a waveform diagram illustrating bipolar pulses which may be used for tissue stimulation.

Instead of stimulating the tissue with unipolar pulses, as shown in line a of FIG. 14, bipolar stimulating pulses 222 shown in line c of FIG. 14, are generated. Such pulses, due to their bipolar nature, significantly reduce the voltage pulse decay time through the saline solution, as represented in lines c and d by 222a. Thus, effectively, the level on the electrode leads tends to return to its quiescent state immediately after each stimulating pulse terminates. Therefore, the biopotential signal 221 following each bipolar pulse 222 is not masked by the stimulated voltage pulse and is impressed without distortion on the same leads, which are used to apply the stimulating pulse 222 to the electrodes for tissue stimulation.

To apply bipolar pulses to tissue instead of unipolar pulses, all that is required is to apply a bipolar voltage source from a bipolar pulse generator not shown, to one end of the resistor 225 in FIG. 13, in place of a voltage from the up converter 17. Bipolar pulse generators are well known and thus need not be described here.

FIG. 15 is a block schematic diagram illustrating details of the selector 38, shown in FIG. 1. It should be recalled that the selector can select words from memory and analog signals from other parts of the HTS, which it is desired to transmit to the outside world, as well as, signals from the tissues, as instructed by a select control word. Assume that, as shown in FIG. 5, each word in the memory has 4 bits respectively designated as $x_1$ through $x_4$. Assume further that each word stored in memory is differentiated by designations $M_{p_1}$-$M_{p_8}$, so that if it is desired to refer to the first digit of the first word this would be designated as $M_{p_1 x_1}$. If it is desired to refer to the fourth digit of the third word this would be designated as $M_{p_3 x_4}$.

There are four digitally controlled switches respectively 230, 232, 234 and 236. Each one of these will have as many input terminals as there are words in memory. Assuming that there are 8 words stored in memory, then each one has at least 8 input terminals. The input terminals of the digitally controlled switch 230 are respectively connected to receive digits $Mp_1x_1$ through $Mp_8x_1$. Switch 232 will have its input terminals respectively connected to the bits $Mp_1x_2$-$MP_8x_2$. The switch 234 will have its input terminal connected to the bits $Mp_1x_3$ to $Mp_8x_3$. The switch 236 will have its input lines connected to receive the bits $Mp_1x_4$-$MP_8x_4$. The one of the input terminals selected by the digitally controlled switches for output is determined by the digital word which is applied to lines 239. This select word comprises the bits $Mp_8x_1$-$MP_8x_4$. Accordingly, the output of the switches 230, 232, 234 and 236 will be 4 bits representing a word determined by the select word.

These 4 bits are applied by the digitally controlled switches in parallel to the 4 stages of a shift register 238, which follows an input stage. The input stage, here designated as $S_1$ has a one applied thereto by a clock signal. This "one" serves as a beginning signal to the circuitry which will respond to this word. In this instance the transmitter is informed that a word for transmittal follows. A shift register 238 is of the kind which can have a parallel input and a serial output. This shift register, upon having the selected digital word entered, commences to shift out the word through the shift stage $S_1$. Further details for this are described in connection with FIG. 16. Another digitally controlled switch, 240, has at least 12 input terminals. Its first 8 input terminals are connected together and receive the output of the shift register 238. The common terminal connects to an amplifier 242, the output of which goes to an RF transmitter. This is the transmitter 32 shown in FIG. 1. The gain of the amplifier 242 is under the control of a digitally controlled selector switch 244.

The gain of the amplifier 242 is established in response to a gain control word applied to the digitally controlled switch 244 from the line 239. One of a plurality of resistors respectively 244-1 through 244-n is selected by the switch 244 and is connected into the gain control network of the amplifier 242. From the foregoing it may be seen how the HTS, which is an embodiment of this invention, can select a word out of memory for retransmission so that it may be checked by the doctor.

Digitally controlled switch 240 and another digitally controlled switch 246 are used for connecting to other portions of the body for external signal transmission. As was previously described, the amount of current flowing to the electrodes over lines 15a and 15b, for example is monitored by measuring the voltage drop across a resistor R and transmitting this value outwardly from the body. Terminal 9 of the switch 240 is connected to one end of the resistor R. Terminal 9 of switch 246 is connected to the other end of resistor R. Accordingly, by applying a proper digital word from lines 238 to switches 240 and 246, the input to these switches is connected across resistor R. The output from these switches is connected to the input of amplifier 242 which has its output connected to the RF transmitter 32.

Terminals 10 of the respective switches 240 and 246 are connected to lines 15a and 15b, and thus when the switches are actuated to select terminal 10, the voltage applied to the electrodes by lines 15a and 15b is transmitted outwardly of the body.

Terminal 11 of switch 240 is connected to the output of amplifier 40, and terminal 11 of switch 246 is connected to the ground. Accordingly, when terminal 11 is selected, the biological signal which the tissue produces is transmitted outwardly from the body. The transmitter can transmit analog as well as digital signals. The biological signal obviously is an analog signal.

Terminal 12 of switch 240 is connected to a reference potential source and terminal 12 of switch 246 is connected to ground. Accordingly, when it is desired to test the gain of amplifier 242, switches 240 and 246 are instructed to select terminals 12 whereby the amplitude of the signal which the transmitter sends is an indication of the gain of amplifier 242. A similar arrangement may be used for connecting a reference potential to amplifier 40 whereby its gain may be checked.

From the foregoing it should be understood how the selector may be instructed to select signals within the body which it is desired to transmit outside of the body for corroboration or for monitoring.

FIG. 16 shows an arrangement for producing register shift pulses and turning on the transmitter. A detector 250, when it senses the presence of select word on the lines 239, provides an output which causes a one shot circuit 252 to provide an output pulse. The output pulse is applied to stage $S_1$ causing it to store a one. The output pulse is also wide enough or provides a sufficient interval so that a shift pulse source 254 can shift out contents of the shift register 238. The transmitter is also turned on by the output of the one shot 252.

When a word for selecting a signal level from the HTS or from tissue is detected by the detector 250, it causes another one shot 256 to provide an output pulse, which enables the transmitter to stay on long enough so that the signal which is selected can be transmitted.

As previously described in connection with FIG. 3a each parameter word is assumed to include the four bits of the parameter value, which are then stored in the parameter memory, defined by the three bits of the parameter type, whenever the parameter word is found to be proper. It was further assumed that whenever a parameter value is stored in its proper memory it replaces the previous parameter value stored therein and thereby controls the particular parameter, e.g., frequency, etc. In accordance with one aspect of the present invention, preferably the parameter values of each parameter are chosen so that the pulse properties change logarithmically rather than linearly for each change of one unit of the parameter value. It is believed that logarithmic changing of the pulse properties is more compatible with the physiological phenomena of the body. Furthermore, although not stated, it was assumed that the value of any parameter which is entered or stored in a memory is independent of the previous parameter value stored in the same memory. Thus, an increase of several units of the parameter value may take place and thereby result in a significant change of the particular pulse property being controlled. Circuits providing logarithmic repsonse to an analog input are well known. Alternatively the logarithm of a digital parameter value can be converted to its logarithm value using a read only memory which provides these conversions. The logarithmic value may then be processed in the manner described herein for signals which are not logarithms.

The present invention is not intended to be limited to such a memory content changing arrangement. If desired, the memory control circuitry may be chosen so that every new parameter used which is received, either increments or decrements the particular parameter value stored in its related memory by one value unit only, either up or down, rather than change the value abruptly by more than one unit of value. That is, if desired the memories may be controlled to ramp up or down in response to the received parameters. As is appreciated by those familiar with the art, the content of a memory, such as a specific address therein, may be changed completely in response to a new entry for the particular address or ramp up or down by one unit in response to each subsequent entry. Thus, the specific memory control circuitry will not be described in detail.

In accordance with the present invention, if desired, each parameter word may include several additional bits which are decodeable by the memory control circuitry to determine whether the content of a memory should be replaced completely by the four parameter bits of the parameter value in the word, or whether the memory content should be ramped up or down. This aspect may be explained in connection with FIG. 3c which is similar to FIG. 3a except that it is shown to further include two additional bits, which define the mode of memory entry. For explanatory purposes if the two bits are both in the 0 state, i.e., 00, it may be used to indicate that the four bits of the parameter value should be substituted for the present parameter value in the particular memory. On the other hand, if these two bits are in a 01 state it may indicate that the four bits of the parameter value are to be ignored and simply ramp the stored parameter value by increasing its existing value by 1. On the other hand, if these two bits are in a 10 state the four bits of the parameter value may be ignored again and the content of the particular memory ramped down by 1 unit. Techniques for such ramping are well known. For example the word at an addressed location is read out and incremented by a unit using an arithmetic circuit, and then written back into the memory.

With such an arrangement, a doctor may, by means of the external controller 22, vary any parameter stored in any of the memories by a significant amount, by sending a parameter word with the three bits of the memory entry mode in the 00 state, or merely cause the parameter value to ramp step-wise, either up or down by sending a parameter word in which the memory entry mode bits are either 01, so as to ramp up, or 10, so as to cause the memory to ramp down by 1. Changing a parameter value abruptly is believed to be advantageous whenever an HTS has to be completely reprogrammed. However, causing the parameters to ramp may be advantagoeus whenever the stored parameter value is close to the desired value, except that it needs minor adjustment. It would also be pointed out that ramping may be advantageous in order to gradually vary any parameter from one value to another rather than do that abruptly. Furthermore, if desired the memories may be controlled so that they can only ramp up or down.

Figure 17:
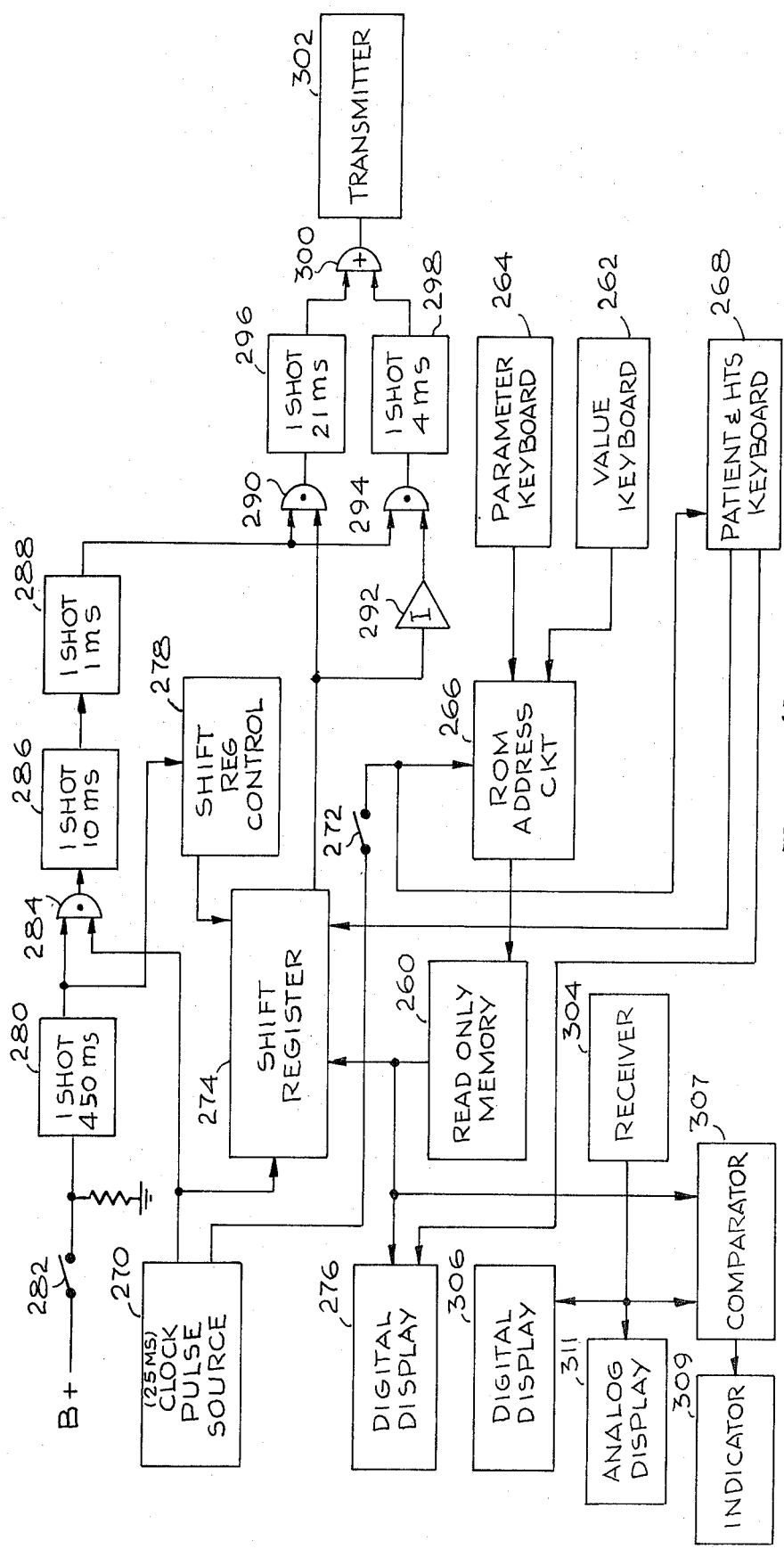
FIG. 17 is a block schematic diagram of a controller, which may be used with this invention.

Referring now to FIG. 17, there is shown a schematic diagram of the external controller 22. It will be recalled that the external controller is the device that the doctor uses to produce the words that are fed into the receiver for transmission to the implanted HTS. A read only memory 260 stores all of the words as well as instructions that are to be supplied to the HTS. This is to be considered as illustrative only, since switch arrangements or keyboard arrangements for generating words may also be used.

A value keyboard 262 has a set of keys thereon, which may be actuated to provide signals representing amplitudes or pulse widths or pulse duration, etc. whch it is desired to have entered into the HTS. A parameter keyboard 264 has keys thereon for indicating which parameter is to have the value which is established by the value keyboard. The signals generated by the parameter and value keyboards are applied to an ROM address circuit 266, which, when actuated, addresses the read only memory 260, which in response reads out a word which has the parameter format and value specified by the keyboards 262 and 264.

For entering patient and HTS data, another keyboard 268 is provided.

A source of clock pulses 270, applies these clock pulses to entry switch 272. When switch 272 is actuated it applies clock pulses to the ROM address circuit 266, causing it to address the read only memory 260, and it also applies clock pulses to the patient and HTS data keyboard causing a read out therefrom of the values which were set when its keys were actuated. The output from the read only memory and from the patient and HTS data keyboard are transferred to a parallel entry serial out shift register 274. The data in the shift register will have a format arrangement such as is represented in any one of FIGS. 3a, 3b or 3c. Outputs from the read only memory and the patient and HTS data keyboard 268 are also applied to a digital display device 276, which then displays the information that was transferred into the shift register 274.

It will be recalled, that FIG. 3d is illustrative of the zero and one pulse waveforms which are transmitted to the implanted HTS, which waveforms are filtered or tested by the circuitry shown in FIG. 4. The description that follows illustrates how the circuits shown in FIG. 17, which are in the controller, provide such waveforms. The values which will be given subsequently, should be considered by way of illustration and not as a limitation upon the invention. The clock pulse source provides an output pulse train comprising a pulse every 25 milliseconds. It is intended that a zero representative pulse will comprise a 4 millisecond pulse at the front end which is at a one level followed by 21 milliseconds at a zero level. A one representative pulse will have a front end which is at a one level for 21 milliseconds followed by 4 milliseconds at a zero level. The clock pulses which occur every 25 milliseconds are very narrow, substantially one microsecond in duration. The shift register 274 is controlled by gates, here designated as shift register control 278 which, when they receive a one pulse input cause the shift register to go from its parallel entry mode to a serial shift out mode. Arrangements for controlling a shift register so that it is transferred from a parallel in to a serial out mode of operation are well known.

A one shot circuit 280, when actuated by a switch 282, hereafter called a transmit switch, applies an output pulse to the shift register control 278, which has a pulse width wide enough so that the shift register control 278 maintains the shift register 274 in its serial out mode long enough to transmit out its contents. The clock pulse source 270 applies pulses to the shift register 274 which cause it to shift out its contents. The width of the output pulse of one shot 280 is on the order of 450 milliseconds which is ample to insure that the shift register can transfer out all of its contents. It should be noted that the pulses from the clock pulse source, when the shift register is in its parallel mode, serve to enter the data which is applied thereto from the read only memory and from the patient and HTS data keyboard.

The output of the one shot 280 is also applied to an And gate 284. Another input to this And gate comprises pulses from the clock pulse source 270. Accordingly, the output from And gate 284, during the interval that the shift register is transferring out its contents, will comprise a train of clock pulses. These clock pulses are applied to a one shot circuit 286, which produces at its output clock pulses which are 10 milliseconds wide. The output of the one shot 286 is applied to a one shot 288, which in response produces one millisecond wide output pulses. The output from one shot 288 comprises a one millisecond pulse delayed 10 milliseconds from each clock pulse.

The output of the shift register 274 is being clocked out by clock pulses which are 25 milliseconds apart. The shift register output is applied to an And gate 290 and to an inverter 292, whose output is applied to a second And gate 294. A second input to each one of these And gates is the output of one shot 288. Accordingly, if the shift register output is a one, And gate 290, 10 milliseconds after a shift register output is applied thereto will provide an output pulse to a one shot 296, which in response provides a pulse having a 21 millisecond width. If the shift register output is zero, then 10 milliseconds after the occurrence of the clock pulse which shifted out the zero, And gate 294 produces an output which is applied to a one shot 298, which in response thereto supplies a 4 millisecond wide pulse output. The outputs from the one shots 296 and 298 are applied to an Or gate 300, which then applies its output to the transmitter 302 to be transmitted.

In effect, when the shift register output is zero, a 4 millisecond wide pulse is transmitted followed by 21 milliseconds at 0 level. Upon the occurrence of the next clock pulse, if the shift register output is zero, the same transmission will occur as has just been described. If the next shift register output is a one, then And gate 290 is actuated by the occurrence of the output of one shot 288. Consequently, one shot 296 is activated and it provides a high output for 21 milliseconds. This is followed by 4 milliseconds during which the output gate 300 is low. Thus the 1's and 0's in register 274, when transmitted by transmitter 302, have the waveforms, shown in FIG. 3a.

A receiver 304 receives the digital and analog data transmitted by the HTS transmitter 32 and applies it to another digital display 306 whereby the two digital displays, 276 and 306 may be compared to determine whether the data stored in memory is in accordance which the data which has been transmitted. Also the digital display 306 can display any of the other digital signals which the internal selector 38 is instructed to select and apply to the transmitter 32 external transmission. If desired, the two digital display inputs may be applied to a comparator 307 which compares its inputs and actuates a light or sound indicator 309 which indicates similarity and/or dissimilarity. An analog display device 311 is also provided. It responds to analog signals which the receiver 304 has received from the HTS, such as the biopotential signals.

Ramping both linear and logarithmic incrementing or decrementing may be carried out by using the keyboards 262 and 264 to insert values into the memory, in response to which incremental or decremental alterations in signal amplitude, or logarithmic changes in signal amplitude may be effectuated.

There are a considerable number of physiological defects and/or diseases in which it is desirable to enable the patient to vary one or more of the parameters in the HTS as well as to be able to turrn the HTS off or on. For example, it may be desirable to enable a patient with an implanted HTS designed to provide stimulating pulses so as to relieve pain, the capability of turning the HTS off when the patient does not experience pain as well as enable the patient to turn the HTS on when pain is felt. Also, since the pain intensity may vary, it may be desirable to enable the patient to vary one or more of the parameters so as to cause the HTS to provide the desired pulses to relieve or at least minimize the pain. Examples of parameters which the patient may want to vary may include pulse frequency and/or pulse amplitude.

Figure 18:
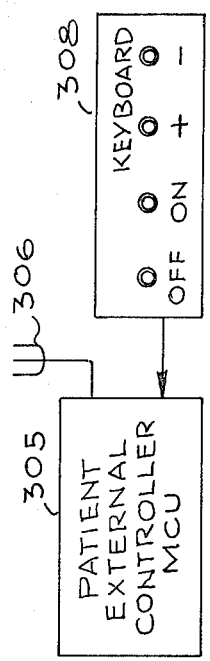
FIG. 18 is a schematic diagram illustrating a patient's controller.

In this connection, attention is directed to FIG. 18. Therein numeral 305 designates a miniature control unit (MCU) with which a patient can control certain aspects of the operation of the HTS. The MCU will have those components of the controller shown in FIG. 17 which are required to perform the limited word generation and transmission to be described. In practice the MCU is made quite small so that it can be held in the patient's hand, or in fact made to be worn like a piece of jewelry such as a bracelet or a watch. The MCU includes an antenna 306 which transmits words, chosen by the patient, to the implanted antenna 25 to control the HTS operation. For example the patient with an operating HTS may desire to turn the HTS off, or turn the HTS on if previously the latter was turned off.

Figure 19:
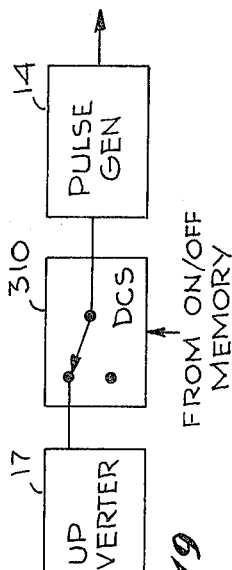
FIG. 19 is a circuit diagram illustrating how the power of an implanted HTS may be controlled from outside of the body.

A keyboard 308 is provided including an on key and an off key. By pressing the on or off key the MCU transmits via its antenna 306 a specific on or off word to the HTS. A special on/off memory (set of flip flops) is provided in the memory 35. As may be seen in FIG. 19, the on or off word is applied to a digitally controlled switch 310 which can either connect the up converter to the pulse generator turning it on or disconnecting the up converter from the pulse generator, turning it off. It should be pointed out that once the pulse generator is reactivated the HTS operates based on the stored parameter values, which a doctor previously programmed.

In addition to being able to turn the HTS on or off the MCU 305 and keyboard 308 may include means to enable the patient to vary at least one parameter, e.g., pulse amplitude by varying the value in the amplitude memory. The pushbutton labelled "+" performs this function. Preferably the amplitude words which may be transmitted from the MCU to the HTS should be of the type which cause memory ramping. This is believed to be highly desirable to prevent the patient from accidentally changing the stored amplitude parameter very significantly which may effect the amplitude of the stimulating pulse to an extent which may be harmful to the patient.

If desired, the "+" or "−" buttons on the keyboard may be connected to circuits which, when the switch is held down, will change the amplitude parameter at a predetermined rate. This can be done for example by enabling an oscillator to apply pulses to a counter whose count output acts as the amplitude control word, or which addresses a ROM with its count output to obtain the amplitude control word. Other parameters may be varied by the patient in this manner, if desired. Rate of ramping can be a controlled oscillator, and instead of a pushbutton use a potentiometer with a voltage applied there across, the output from which is applied to the voltage controlled oscillator.

It should be clear that the MCU which is provided to any patient must generate each parameter word with the proper identification bits, namely the model number of the HTS and the patient's particular number. The MCU may be provided with an externally adjustable dial or other means to enable a doctor to permanently set the model number and the patient number to correspond to those in the implanted HTS. The inclusion of a patient number in each parameter word may be particularly important to prevent patients with their different MCU's from activating the HTS's of each other. For example, several patients with implanted HTS's may be present in a doctor's waiting room. In such a case it would be of paramount importance to prevent any patient from affecting the parameters in the HTS's of the other patients when operating his MCU in order to vary the parameter(s) in his HTS.

Under normal circumstances, the doctor treating a patient with an implanted HTS would know both the patient's number and the model number of the implanted HTS, so that the external controller may be set to provide the proper identification bits with each parameter word. However, to provide maximum flexibility and enable a doctor, who may not know either the HTS's model number or the patient's number, to program the HTS in the absence of the patient's regular doctor or under emergency conditions, when such information cannot be obtained from the patient himself, who may be in a coma. Such a capability can be provided with an HTS in which it is assumed to include the following features. As may be seen in FIG. 5, the HTS model number in unit 60 and the patient number in unit 66 may be selected by the selector 38. These two numbers, each of 3 bits may be viewed as one 6-bit number, which the selector can provide to the transmitter 32 when an appropriate read parameter value from the read memory is applied to the selector via line 36.

Figure 20:
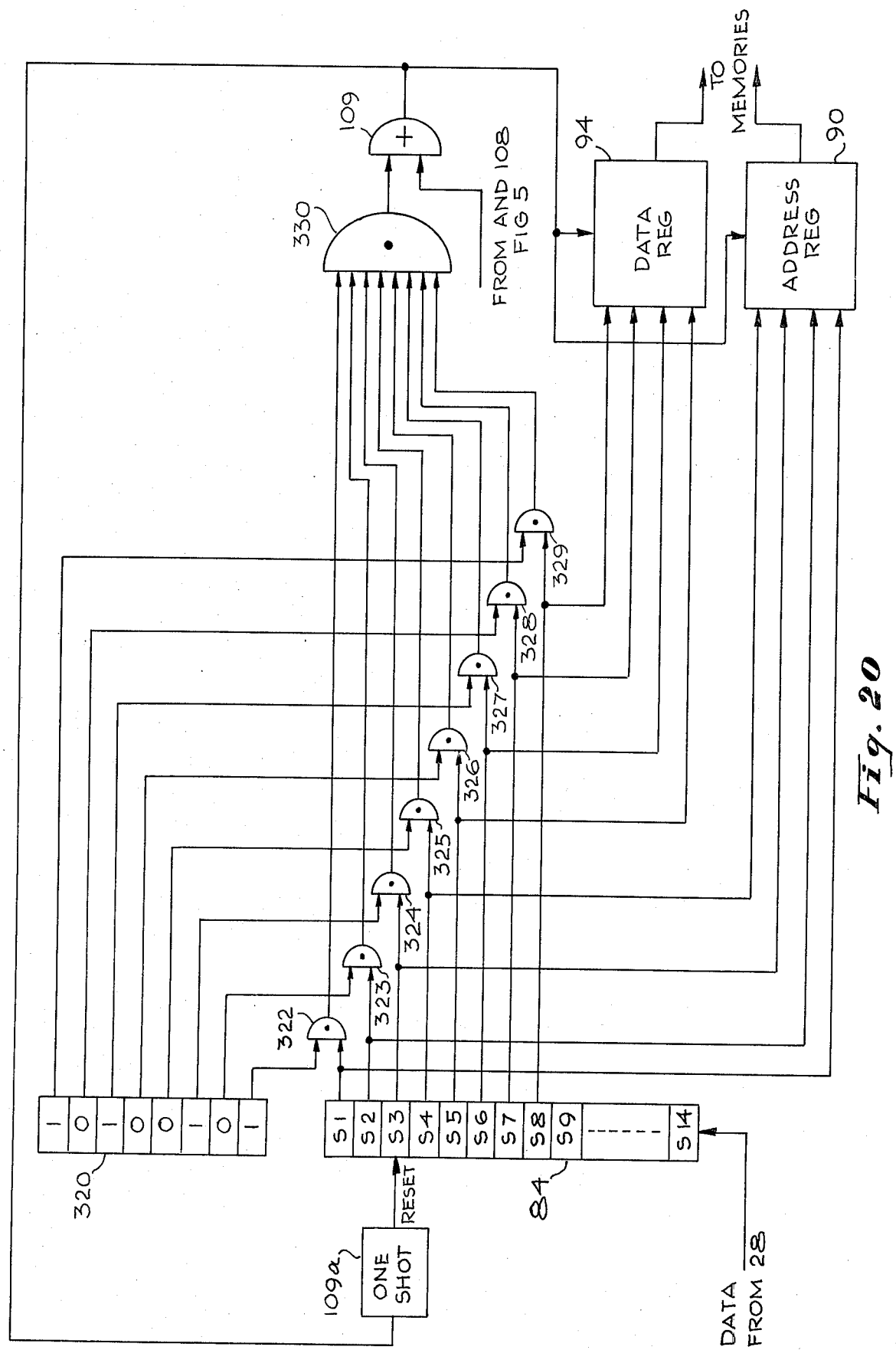
FIG. 20 is a schematic diagram of circuits which may be used to insure that the signals transmitted to the HTS are for the intended HTS.

Referring now to FIG. 20 there is shown a schematic of an arrangement for enabling readout of HTS and patient numbers from the HTS. This circuit includes components shown in FIG. 5 which will have the same reference numerals as are provided in FIG. 5. The circuit of FIG. 5 can include a register 320 in which a particular 8 bit read parameter word is permanently stored. It includes the start 1 bit, 3 bits which define the specific read memory, which for explanatory purposes are assumed to be 010, and 4 bits which define the specific read parameter necessary to activate the selector 38 to read out the HTS model and patient numbers. These 4 bits are assumed to be 1010. Thus, the unit 320 stores the bits 10100101 (from right to left). The content of unit 320 is compared by And gates 322-329 with the contents of stages S1-S8 of register 50.

The doctor who does not know the HTS model and patient number transmits the special read parameter word 10100001 to the HTS followed by 6 bits whose binary levels are not important. It should thus be clear that when these 14 bits are received and clocked into register 84 bits 10100101 are present in stages S1-S8. Consequently, all the outputs of comparators 322-329 are high therefore an And gate 330 is enabled, which in turn enables Or gate 109. The latter activates the registers 90 and 94. Thus, the special read parameter 1010 is loaded in the read memory at address 010. This read parameter is supplied from the read memory to the selector 38 which enables the HTS model and patient numbers to be supplied to the transmitter 32 for transmission to the external controller wherein they are displayed. Once these numbers are known the doctor may control the controller to send them as the six identification bits at the end of each parameter word which is sent to the HTS to program the latter.

The HTS model and patient numbers may be stored in two separate memories such as a model number memory and a patient number memory rather than fixedly stored in units 60 and 66. The outputs of these two memories would then be used in screening each parameter word to insure that it ends with the proper identification bits. In such an arrangement the doctor may at any time vary either of these numbers by sending an appropriate parameter word, in the same way that the parameter in each of the other memories is varied as hereinbefore explained. Such a flexibility may be desirable, to simplify the HTS fabrication. All HTS's may be fabricated without having to preset the HTS model and patient numbers to specific values. Rather they are set to all zero. These numbers would then be set by the doctor either before or after the HTS is implanted to specifically chosen values. This would help prevent two patients of the same doctor from having identical patient numbers.

In the above description it was assumed that the read parameter controls which signals (parameter or analog signals) are transmitted from the HTS. Thus the signals which are received by the external controller may not necessarily be indicative of the content of the last word which was transmitted to the HTS. If desired, once a word is verified in decoder 30 as proper and the write signal is produced, thr latter may be used to turn on the transmitter to transmit the parameter type bits such as those in stages S2-S4 of register 50 and the parameter value bits, such as those in stage S5-S8 to the external controller. Thus in such an arrangement the parameter related bits last transmitted by the external controller are returned to it if they are contained in a properly received parameter word. It should be understood that this is included in the invention.

Furthermore, if desired, following the transmission of the parameter related bits of the last received word, signals responsive to the value defined by that parameter may be transmitted out. The reception, first, of the parameter related bits can be used to verify the proper operation of the decoder and the reception of the signals responsive to the parameter value may be used to verify the proper operation of the memories. Clearly various known circuits may be used to cause the selector to select which signals are to be applied to the transmitter for transmission to the external controller.

Although particular embodiments of the invention have been described and illustrated herein, modifications and variations may readily occur to those skilled in the art. Consequently, it is intended that the claims herein be interpreted to cover such modifications and equivalents.

I claim:

1. A programmable human tissue stimulator system comprising:
    an implanted stimulating signal generator for generating body tissue stimulating pulses responsive to control signals,
    an implanted memory means for storing control signals for controlling said stimulating signal generator, external control means for generating a plurality of sets of signals, each set including control signals, and signals which represent a memory address in said memory means, external means for transmitting said generated sets of signals;

an implanted receiver for receiving said sets of transmitted signals, implanted means for verifying that the received signals in each set are accurate and for producing an accurate signal when each signal in a set has substantially either a first waveform or a second waveform, an implanted memory address means for storing the memory address which is represented by the memory address representing signal in the set;

implanted means responsive to said accurate signal for entering selected ones of the received control signals in each set in the memory means at the memory address stored in said memory address means, and implanted means for controlling said implanted stimulating signal generator with control signals from said memory.

2. A programmable human tissue stimulator system as recited in claim 1 wherein said means for verifying that the received signals in each set are accurate includes:

means for determining that each set of signals includes identification signals at preselected locations within the set and that each identification signal at its preselected location has a predetermined one of said first and second waveforms.

3. A programmable human tissue stimulator system as recited in claim 1 wherein there is included an implanted transmitter means for external transmission of signals applied thereto, selector means for applying to said implanted transmitter means control signals which are stored in said memory means, external receiver means for receiving the control signals transmitted by said implanted transmitter means, and means for determining that the control signals received by said external receiver means correspond to the control signals generated by said means for generating control signals.

4. A programmable human tissue stimulator system as recited in claim 1 wherein said sets of signals comprise digital words, each digital word including identification bits at preselected locations within said word, said means for verifying includes means for examining said preselected locations to determine the presence or absence of said identification bits.

5. A programmable human tissue stimulator system as recited in claim 1 wherein there is included an implanted transmitter means for external transmission of signals applied thereto, coupling means connecting said implanted stimulating signal generator to the tissue to be stimulated, detecting means connected to said coupling means for detecting the stimulating signal applied by said stimulating generator to said tissue, as well as any electrical signal produced by said tissue, selector means for applying signals detected by said detecting means to said implanted transmitter means, external receiver means for receiving the detected signals transmitted by said implanted transmitter means, and means for diplaying the signals received by said external receiver means.

6. A programmable human tissue stimulator system as recited in claim 1 wherein said means for verifying that the received signals are accurate and producing an accurate signal indicative thereof includes, a second external means for transmitting said generated set of signals, a second implanted receiver for receiving said second set of signals transmitted by said second means for transmitting, and means for comparing the set of signals received by said implanted receiver with the set of signals received by said second implanted receiver and producing said accurate signal if they are identical.

7. A programmable human tissue stimulator system as recited in claim 6 wherein said second external means for transmitting is a modulated light source, and said second implanted receiver is a light to electrical signal transducer.

8. A programmable human tissue stimulator system as recited in claim 1 wherein said external control means includes:

means for generating a first signal for turning off and a second signal for turning on said implanted stimulating signal generator, and implanted switch means for applying operating potential to said implanted stimulating signal generator responsive to said first signal and for discontinuing the application of said operating potential responsive to said second signal.

9. A programmable human tissue stimulator system as recited in claim 1 wherein said external control means includes means for generating successive sets of signals each of which when applied to said implanted stimulating signal generator causes only a predetermined incremental change in said implanted stimulating signal output.

10. A programmable human tissue stimulator system comprising:

an implanted stimulating signal generator for generating body tissue stimulating pulses responsive to control signals, an implanted memory means for storing control signals for controlling said stimulating signal generator, external control means for generating a plurality of sets of signals, each set including control signals, external means for transmitting said generated sets of signals, an implanted receiver for receiving said sets of transmitted signals, implanted means for verifying that the received signals in each set are accurate and for producing an accurate signal when each signal in a set has substantially either a first waveform or a second waveform, implanted means responsive to said accurate signal for entering selected ones of the received control signals in each set in a location in said memory means which is defined by other signals in the set, implanted means for controlling said implanted stimulating signals generator with control signals from said memory, each set of signals comprises a word comprised of binary pulses, each binary pulse rising from a leading edge to a first predetermined amplitude which extends first for a predetermined interval thereafter, then said binary pulse extends for a second predetermined interval at an amplitude level determined by its binary value, and thereafter extends for a third predetermined interval at a second predetermined value, means for determining that each signal has an acceptable waveform includes, first means responsive to the leading edge of a binary pulse for generating a reset pulse responsive to a binary value amplitude level change during said second predetermined interval, and second means responsive to the leading edge of a binary pulse for generating a reset pulse responsive to a change in said first predetermined amplitude during said first predetermined interval, register means into which a received binary word is transferred from said implanted receiver, and means for applying said reset signals to said register means to clear said register means.

11. A programmable human tissue stimulator system comprising:

an implanted stimulating signal generator for generating, responsive to control signals, body tissue stimulating pulse trains having parameters which are determined by said control signals, an implanted memory means for storing, at different locations, different parameter determining control words for determining the parameters of the pulse train output of said stimulating pulse signal generator, external control means for generating digital word signals, each word including a first plurality of binary bits representing a parameter for a pulse train, a second plurality of binary bits representing the storage location of said parameter in memory, and a third plurality of binary bits representing patient identifying data, an external transmitter for transmitting said digital word signals, an implanted receiver for receiving said transmitted signals, an implanted temporary storage means for storing word signals received by said receiver, means for verifying that the waveform of the received binary bits in a word have a predetermined acceptable waveform and clearing said temporary storage if the waveform is not acceptable, implanted means for storing patient identifying data, means for comparing the received patient identifying data with stored patient identifying data and producing an acceptance signal if they are the same, means responsive to said acceptance signal for transferring said first plurality of binary bits, from said temporary storage into the location in memory means indicated by said second plurality of binary bits, and means responsive to said acceptance signal for clearing said temporary storage.

12. A programmable human tissue stimulator system as recited in claim 11 wherein there is included:

an implanted transmitter means for external transmission of signals applied thereto, implanted selector means for selecting for application to said implanted transmitter means signals occurring at predetermined locations within the implanted circuits of said programmable human tissue stimulator system specified by selection signals, said digital word signals generated by said external control means including a fourth plurality of binary bits representative of a selection signal, means for applying a fourth plurality of binary bits received by said implanted receiver to said implanted selector means whereby said implanted transmitter transmits the signals from the location specified, an external receiver for receiving the transmitted signals, and means for utilizing the signals received by said external receiver.

13. A programmable human tissue stimulator system as recited in claim 11 wherein said implanted signal generator includes switch means for applying pulse wavetrains from said stimulating signal generator to tissue at different locations, and means responsive to stored first pluralities of binary bits in said memory for controlling operation of said switch means.

14. A programmable human tissue stimulator system as recited in claim 11 wherein there is included:

a second external transmitter means for transmitting said generated word signals, a second implanted receiver for receiving the signals transmitted by said second external transmitter means, and means for comparing the first and second pluralities of binary bits received by said second implanted receiver, with the first and second pluralities of binary bits in said temporary storage and producing a temporary storage clear signal when they are not alike.

15. A programmable human tissue stimulator system as recited in claim 14 wherein said second external means for transmitting is a modulated light source, and said second implanted receiver is light to electrical signal transducer.

16. A programmable human tissue stimulator system as recited in claim 14 wherein said second external means for transmitting is a means for generating a modulated sound, and said second implanted receiver is a sound to electrical signal transducer.

17. A programmable human tissue stimulator system as recited in claim 14 wherein said second external means for transmitting is a means for generating a modulated magnetic field, and said second implanted receiver is a magnetic field to electrical signal transducer.

18. A programmable human tissue stimulator system as recited in claim 11 wherein said external control means includes means for generating successive control signals each of which when applied to said implanted stimulating signal generator causes only a predetermined incremental change in said implanted stimulating signal output.

19. A programmable human tissue stimulator system as recited in claim 11 wherein each of the pulses of said pulse trains generated by said implanted stimulating signal generator are biphasic pulses.

20. A programmable human tissue stimulator system as recited in claim 11 wherein each of the digital word signals generated by said external control means includes redundant binary bits at predetermined spaced locations in a word, and there is included:

means for verifying the presence of said redundant binary bits at said predetermined locations and preventing said means for comparing producing an acceptance signal when said redundant binary bits are not at said predetermined locations.

21. A programmable human tissue stimulator system as recited in claim 4 wherein said external control means includes:
- means for generating a first signal for turning off and a second signal for turning on said implanted stimulating signal generator, and
- implanted switch means for applying operating potential to said implanted stimulating signal generator responsive to said first signal and for discontinuing the application of said operating potential responsive to said second signal.

22. A programmable human tissue stimulator system as recited in claim 11 wherein there is included an implanted reference level signal source, and
- said external means for generating digital word signals includes means to specify a word signal for instructing said implanted digitally responsive switch means to connect to said implanted reference level signal source, whereby the signal received by said external receiver means will be a calibration signal.

23. A system for obtaining electrical biophysical signals from electrodes placed at a plurality of different tissue locations within a body comprising:
- external means for generating digital word signals specifying a tissue location from which it is desired to obtain electrical biophysical signals,
- an external transmitter for transmitting said digital word signals,
- an implanted receiver for receiving said digital word signals,
- an implanted transmitter for transmitting an electrical biophysical signal,
- implanted switch means responsive to said digital word signals for selectively connecting to said implanted transmitter an electrode placed at a tissue location from among a plurality of electrodes placed at different tissue locations within said body, said location being specified by said digital word signal, whereby said implanted transmitter will transmit electrical biophysical signals from said tissue location, and
- external receiver means for receiving said transmitted electrical biophysical signals.

24. A programmable human tissue stimulator system comprising:
- an implanted stimulating signal generator for generating body tissue stimulating pulses responsive to control signals,
- an implanted memory means for storing control signals, for controlling said stimulating signal generator,
- external control means for generating a plurality of sets of signals, each set including at least control signals, several of said sets further including memory location signals,
- means for transmitting each of said generated sets of signals,
- an implanted receiver for receiving each of said transmitted sets of signals,
- means for verifying that the received signals in each set are accurate and producing an accurate signal indicative thereof only when each signal in the set has substantially either a first or a second waveform,
- means responsive to said accurate signal for entering said received control signals in said memory means, at a location defined by the memory location signals in the set,
- means responsive to certain ones of said control signals in said memory means for controlling said generator to establish the frequency of the body tissue stimulating pulses which it generates,
- means responsive to others of said control signals in said memory means for controlling said generator to establish the periods of bursts of the body tissue stimulating pulses which it generates, and
- means responsive to still others of said control signals in said memory means for controlling said generator to establish the amplitude of the body tissue stimulating pulses which it generates.

25. A programmable human tissue stimulator system as recited in claim 24 wherein said body tissue stimulating pulses are adapted to be applied to more than one body tissue, through plural applicator means,
- said means responsive to others of said control signals in said memory for controlling said generator to establish the periods of bursts of the body tissue stimulating pulses includes means for controlling the timing of the application of said periods of bursts to said plural applicator means which are adapted to apply them to each of said more than one body tissue.

26. A programmable human tissue stimulator system comprising
- an implanted stimulating signal generator for generating, responsive to control signals, body tissue stimulating pulse trains having parameters which are determined by said control signals,
- an implanted memory means for storing, at different locations, different parameter determining control words for determining the parameters of the pulse train output of said stimulating pulse signal generator,
- external control means for generating digital word signals, each word including a first plurality of binary bits representing a parameter for a pulse train, a second plurality of binary bits representing the storage location of said parameter in memory, and a third plurality of binary bits representing identifying data,
- an external transmitter for transmitting said digital word signals,
- an implanted receiver for receiving said transmitted signals,
- an implanted temporary storage means for storing word signals received by said receiver,
- implanted means for storing identifying data,
- means for comparing the received identifying data with stored patient identifying data and producing an acceptance signal if they are the same,
- means responsive to said acceptance signal for transferring said first plurality of binary bits, from said temporary storage into the location in memory means indicated by said second plurality of binary bits, and
- means responsive to said acceptance signal for clearing said temporary storage.

27. A programmable human tissue stimulator system as recited in claim 26 wherein there is included:

an implanted transmitter means for external transmission of signals applied thereto, implanted selector means for selecting for application to said implanted transmitter means signals occurring at predetermined locations within the implanted circuits of said programmable human tissue stimulator system specified by selection signals, said digital word signals generated by said external control means including a fourth plurality of binary bits representative of a selection signal, instructing said selector means to apply the patient identifying word to said implanted transmitter means to be transmitted externally, an external receiver for receiving the transmission of said implanted transmitter means, and means for displaying the identifying word received by said external receiver for verification.

28. A programmable human tissue stimulator system comprising:

an implanted stimulating signal generator for generating, responsive to control signals, body tissue stimulating pulse trains having parameters which are determined by said control signals, an implanted memory means for storing, at different locations, different parameter determining control words for determining the parameters of the pulse train output of said stimulating pulse signal generator, external control means for generating digital word signals, including a plurality of binary bits representing identifying data, an external transmitter for transmitting said digital word signals, an implanted receiver for receiving said transmitted signals, as implanted transmitter, implanted means for storing identifying data, means for comparing the received identifying data with the stored identifying data, and means for selectively connecting said internal transmitter to said implanted means for storing identifying data to selectively transmit said stored identifying data.

29. A programmable human tissue stimulator system comprising:

an implanted stimulating signal generator responsive to different groups of control signals for generating body tissue stimulating pulses having characteristics which are functions of said groups of the control signals;

an implanted memory means for storing in a plurality of locations groups of control signals, for controlling said stimulating signal generator as a function of at least some of said groups of control signals;

external control means for generating any one of a plurality of sets of signals, each set including a group of control signals, some sets further including memory-address-defining signals;

means for transmitting each generated set of signals;

an implanted receiver for receiving said transmitted set of signals;

means for verifying that the received set of signals is accurate and producing an accurate signal indicative thereof, only when each signal in the set has substantially a first or a second waveform;

means responsive to said accurate signal for entering the control signals in the received set in said memory means, at a location, defined by said memory-address-defining signals in said received set, without affecting the control signals located in other locations; and an implanted battery for continuously applying power to at least said generator and said memory means, independent of external power source means.

30. A programmable human tissue stimulator system as described in claim 29 wherein said external control means includes manually carriable and operable external control means for generating at least one of said sets of signals for transmission to said implanted receiver, said at least one set includes a group of control signals for varying at least one characteristic of said stimulating pulses.

31. A programmable human tissue stimulator system as described in claim 30 wherein said one characteristic is pulse amplitude.

32. A programmable human tissue stimulator system as described in claim 30 wherein said one characteristic is pulse frequency.

33. A programmable human tissue stimulator system as described in claim 20 wherein said manually carriable and operable external control means includes means for generating a set of signals which includes control signals for turning said signal generator on or off.

34. A programmable human tissue stimulator system as described in claim 30 further including implanted transmitter means for transmitting to said manually carriable external control means signals indicative of the control signals received therefrom.

35. A programmable human tissue stimulator system as described in claim 24 wherein said manually carriable external control means is adapted to be worn on a patient's wrist or attachable to form part of a patient's wearable item of jewelry.

* * * * *

REEXAMINATION CERTIFICATE (860th)
United States Patent [19]

Schulman

[11] B1 4,232,679

[45] Certificate Issued May 31, 1988

[54] PROGRAMMABLE HUMAN TISSUE STIMULATOR

[75] Inventor: Joseph H. Schulman, Los Angeles, Calif.

[73] Assignee: Pacesetter Systems, Inc., Sylmar, Calif.

Reexamination Request:
No. 90/000,677, Dec. 4, 1984
No. 90/000,700, Dec. 31, 1984

Reexamination Certificate for:
Patent No.: 4,232,679
Issued: Nov. 11, 1980
Appl. No.: 762,626
Filed: Jan. 26, 1977

[51] Int. Cl.$^4$ .............................................. A61N 1/36
[52] U.S. Cl. .................................................. 128/419 PG
[58] Field of Search ........... 128/419 P, 419 D, 419 E, 128/419 PG, 419 PT, 421–423, 631, 668, 670, 696–709, 731; 370/8–10, 18, 60; 371/34, 49, 67

[56] References Cited

U.S. PATENT DOCUMENTS

| | | | |
|---|---|---|---|
| 2,691,154 | 10/1954 | Rajchman | 340/174 |
| 2,785,389 | 3/1957 | Warren | 340/174 |
| 2,887,674 | 5/1959 | Greene | 340/174 |
| 3,156,893 | 11/1964 | Harel | 340/146.1 |
| 3,159,816 | 12/1964 | Tiemann | 340/147 |
| 3,198,195 | 8/1965 | Chardack | 128/419 |
| 3,241,556 | 3/1966 | Zacouto | 128/421 |
| 3,299,424 | 1/1967 | Vinding | 343/6.5 |
| 3,436,813 | 4/1969 | Wells et al. | 29/604 |
| 3,478,344 | 11/1969 | Schwitzgebel et al. | 340/312 |
| 3,582,786 | 6/1971 | Bruglemans | 325/41 |
| 3,594,500 | 7/1971 | James et al. | 178/22 |
| 3,594,585 | 7/1971 | Bourget | 307/234 |
| 3,639,907 | 2/1972 | Greatbatch | 340/150 |
| 3,662,758 | 5/1972 | Glover | 128/419 E |
| 3,665,417 | 5/1972 | Low et al. | 340/172.5 |
| 3,680,050 | 7/1972 | Griffin | 340/167 R |
| 3,693,627 | 9/1972 | Berkovits | 128/419 P |
| 3,718,909 | 2/1973 | Greatbatch | 340/167 A |
| 3,719,890 | 3/1973 | Borciani et al. | 325/55 |
| 3,720,926 | 3/1973 | Wolff | 340/174.1 H |
| 3,727,142 | 4/1973 | De Sipio et al. | 328/111 |
| 3,747,067 | 7/1973 | Fox et al. | 325/41 |
| 3,751,718 | 8/1973 | Hanchett, Jr. | 317/134 |
| 3,774,594 | 11/1973 | Huszar | 128/706 |
| 3,774,619 | 11/1973 | Goldberg | 128/419 P |
| 3,805,796 | 4/1974 | Terry, Jr. et al. | 128/419 P |
| 3,806,874 | 4/1974 | Ehrat | 340/149 R |
| 3,813,530 | 5/1974 | Chevalier et al. | 235/153 A |
| 3,867,950 | 2/1975 | Fischell | 128/419 P |
| 3,872,437 | 3/1975 | Cross | 340/147 SY |
| 3,882,260 | 6/1975 | Fischell | 128/419 PG |
| 3,882,470 | 5/1975 | Hunter | 340/173 R |
| 3,885,552 | 5/1975 | Kennedy | 128/419 PT |
| 3,898,984 | 8/1975 | Mandel et al. | 128/696 |
| 3,906,348 | 9/1975 | Willmott | 325/37 |
| 3,952,750 | 4/1976 | Mirowski et al. | 128/419 D |
| 3,995,225 | 11/1976 | Horn | 329/106 |
| 4,026,305 | 5/1977 | Brownlee et al. | 128/419 PT |
| 4,049,004 | 9/1977 | Walters | 128/419 PG |
| 4,059,749 | 11/1977 | Feilchenfeld | 235/302 |
| 4,082,097 | 4/1978 | Mann et al. | 128/419 PS |
| 4,087,753 | 5/1978 | Paul | 325/38 R |
| 4,151,831 | 5/1979 | Lester | 128/736 |
| 4,275,739 | 6/1981 | Fischell | 128/419 PG |
| 4,304,238 | 12/1981 | Fischer | 128/419 PG |

OTHER PUBLICATIONS

Miller, H. A. et al, "Biomedical Applications of Aerospace Technology", Proceedings of the San Diego Biomedical Symposium, 1973, vol. 12, San Diego, Calif., Jan. 31–Feb. 2.

Preliminary Technical Manual for XYTRON-RA ™ Pulse Generators Models 5954, 5955-MC75026a-Medtronics, Inc.

Fischell, R. E. "Down to Earth Space Benefits Result from Moon Missions", Space World Jan. 1975.

"The Omnicor System–A New Generation of Cardiac Pacers", by Cordis Corporation.

Hardage, M. L.; Barold, S. S.; "Pacemaker Programming Techniques"; The Third Decade of Cardiac Pacing (Futura Pub. Co., N.Y., 1982) pp. 1–26.

Lister; "The Fourth Decade of Pacing"; The Third Decade of Cardiac Pacing (Futura Pub. Co., N.Y., 1982) 00. 479–487.

"A Programmable Sampling Format Telemetry System", Max R. Peterson, Proceedings 1973 International Telemetering Conference, 1973, Conference Date: Oct. 9–11, 1973.

"The Small Astronomy Satellite (SAS) Program", Marjorie R. Townsend, Proceedings 1968 International Telemetering Conference, 1968, Conference Date: Oct. 8–11, 1968.

APL Technical Digest, vol. 14, No. 4, Oct.–Dec. 1975.
APL Technical Digest, vol. 10, Nos. 4 and 5, Mar.–Jun. 1971.
APL Technical Digest, vol. 14, No. 3, Jul.–Sep. 1975.
Applied Physics Laboratory Technical Memorandum, "The Small Astronomy Satellite Command Encoder", A. J. Pokorny, T. G.-1065, Mar. 1969.

Medtronic External Rate Control Model 5855 Technical Information Manual, May 1968.

(List continued on next page.)

*Primary Examiner*—William Kamm

[57] ABSTRACT

An implanted heart and tissue stimulator is provided which is externally programmable so that stimulating signals generated thereby can be changed to meet the changing requirements of the user. Provision is made for verifying and screening control parameter words which are transmitted from an external controller so that only correct parameters will be stored for use by the implanted stimulator. Provision for read out of stimulating signals and of the tissue response thereto is also provided.

OTHER PUBLICATIONS
(See Top Sheet)

"An Implantable Multichannel Biotelemetry System" by J. D. Pauley et al, Electroencepholography and Clinical Neurophysiology, 1974, 37: 153–160, printed in the Netherlands.

"A Synchronized Discrete Address Beacon System" by N. A. Blake, Proceedings of the 1973 International Telemetering Conference, copyright 1973, Conference date Oct. 9–11, 1973.

"The Interrogation, Reporting and Location System Experiment", J. R. Cressey et al, Proceedings of the 1965 National Telemetering Conference, copyright 1965, presented Apr. 14, 1965.

"The Incorporation of a Magnetic Switch Into an Implanted Pacemaker", J. Weinman, Journal of Thoracic and Cardiovascular Surgery, 48:690–692, 1964.

"A Permanent Pacemaker Capable of External Noninvasive Programming" V. Parsonnett et al, vol. XIX Transactions of The American Society for Artificial Internal Organs, 1973, pp. 224–228.

"Coding For Error Free Communications", A. G. Franco, Electro-Technology Science and Engineering Series, No. 109, Jan. 1968.

"Data Reliability", S. G. Powers, Proceedings 1973 International Telemetering Conference, 1973, Conference dates: Oct. 9–11, 1973.

"Electronics in the Telstar Satellite", R. C. Chapman et al, New Links to New Worlds, 1963 National Space Electronic Symposium, held Oct. 1–4, 1963 at the Hotel Fontainbleu in Miami Beach, Florida, copyright 1963.

"Implantable ECG Transmitter Employing a Magnetic Switch", E. N. Smith et al, Journal of Applied Physiology, vol. 36, No. 5, May 1974.

"Implant Biotelemetry and Microelectronics", W. H. Ko et al, Science 156 (773): 351–360, Apr. 21, 1967.

Xytron-RA Rate Controller Model 9600-MC 74512, Physician Manual, Oct. 1974.

"Controlled External Powering of Miniaturized Chronically Implanted Biotelemetry Devices", R. Kadefors, IEEE Transactions on Biomedical Engineering, vol. BME-23, No. 2, Mar. 1976.

"A Remote Control Brain Telestimulator with Solar Cell Power Supply", H. Warner et al, IEEE Transactions on Biomedical Engineering, vol. BME-15, No. 2, Apr. 1968.

"Remote Switching with Latching to Selected Sites of Variable Sequency Cardiac Pacing", E. J. Reininger et al, Journal of Applied Physiology, vol. 29, No. 6, Dec. 1970, pp. 889–891.

"A Long-Lived, Reliable, Rechargeable Cardiac Pacemaker" by R. E. Fischell, K. B. Lewis, J. H. Schulman, and J. W. Love, pp. 357–382 of *Advances in Pacemaker Technology* edited by M. Schaldach et al, Springer-Verlag, 1975.

"Rechargeable Cardiac Pacemaker" by William E. Chapman, III, MD, pp. 235–236, Postgraduate Medicine, Oct. 1973, vol. 54, No. 4.

"Bridge to the Medical World: Biomedical Applications of Space Technology (Film), by E. Schmidt, MD, Stanford University, Sponsor: Cardiology Division of the Stanford University Medical School and NASA, produced by Film Media, Inc., 1975.

"An Implantable Monolithic Command Receiver" by Hudson et al, presented at the 8th International Conference on Medical and Biological Engineering and the 22nd Annual Conference on Engineering in Medicine and Biology in 1969, Chicago, Illinois.

"An Integrated Nonvolatile Read-Write Memory with Addressing" by H. A. R. Wegner et al, presented at the 1969 National Aerospace Electronics Conference in Dayton, Ohio, Abstract at p. 433 of the proceedings of the 1969 National Aerospace Electronics Conf.

"Pacing Sustems Price List-Apr. 1975", by Cordis Corporation, pp. 1–11.

"San Francisco Rounds", by Alan M. Kennedy, Medical World News, 10/8/71, p. 76.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 27, lines 40-55:

Referring now to FIG. 20 there is shown a schematic of an arrangement for enabling readout of HTS and patient numbers from the HTS. This circuit includes components shown in FIG. 5 which will have the same reference numerals as are provided in FIG. 5. The circuit of FIG. 5 can include a register 320 in which a particular 8 bit read parameter word is permanently stored. It includes the start 1 bit, 3 bits which define the specific read memory, which for explanatory purposes are assumed *to be 010*, and 4 bits which define the specific read parameter necessary to activate the selector 38 to read out the HTS model and patient numbers. These 4 bits are assumed to be 1010. Thus, the unit 320 stores the bits 10100101 (from right to left). The content of unit 320 is compared by And gates 322-329 with the contents of stages S1-S8 of register [50] *84*.

Column 28, lines 7-25:

The HTS model and patient numbers may be stored in two separate memories such as a model number memory and a patient number memory rather than fixedly stored in units [60 and 66] *100 and 106*. The outputs of these two memories would then be used in screening each parameter word to insure that it ends with the proper identification bits. In such an arrangement the doctor may at any time vary either of these numbers by sending an appropriate parameter word, in the same way that the parameter in each of the other memories is varied as hereinbefore explained. Such a flexibility may be desirable, to simplify the HTS fabrication. All HTS's may be fabricated without having to preset the HTS model and patient numbers to specific values. Rather they are set to all zero. These numbers would then be set by the doctor either before or after the HTS is implanted to specifically chosen values. This would help prevent two patients of the same doctor from having identical patient numbers.

AS A RESULT OF REEXAMINATION, IT HAS BEEN DETERMINED THAT:

Claims 22-35 are cancelled.

Claims 1, 2, 6, 10, 11, 14, 15 and 21 are determined to be patentable as amended.

Claims 3-5, 7-9, 12, 13, and 16-20, dependent on an amended claim, are determined to be patentable.

New claims 36 and 37 are added and determined to be patentable.

1. A programmable human tissue stimulator system comprising:
   an implanted stimulating signal generator for generating body tissue stimulating pulses responsive to control signals,
   an implanted memory means for storing control signals for controlling said stimulating signal generator,
   external control means for generating a plurality of sets of signals, each set including control signals, and signals which represent a memory address in said memory means,
   external means for transmitting said generated sets of signals;
   an implanted receiver for receiving said sets of transmitted signals,
   implanted means for verifying that the received signals in each set are accurate and for producing an accurate signal when each signal in a set has substantially either a first waveform or a second waveform,
   an implanted [memory address] *temporary storage* means for storing the memory address which is represented by the memory address representing signal in the set[;] *in response to the generation of said accurate signal*,
   implanted means [responsive to said accurate signal] for entering selected ones of the received control signals in each set in the memory means at the memory address stored in said [memory address] *temporary storage* means, and
   implanted means for controlling said implanted stimulating signal generator with control signals from said memory.

2. A programmable human tissue stimulator system as recited in claim 1 wherein said means for verifying that the received signals in each set are accurate *further* includes:
   means for determining that each set of signals includes identification signals at preselected locations within the set and that each identification signal at its preselected location has a predetermined one of said first and second waveforms.

6. [A programmable human tissue stimulator system as recited in claim 1 wherein said means for verifying that the received signals are accurate and producing an accurate signal indicative thereof includes,] *A programmable human tissue stimulator system comprising:*
   *an implanted stimulating signal generator for generating body tissue stimulating pulses responsive to control signals,*
   *an implanted memory means for storing control signals for controlling said stimulating signal generator,*
   *external control means for generating a plurality of sets of signals, each set including control signals, and signals which represent a memory address in said memory means,*
   *external means for transmitting said generated sets of signals;*
   *an implanted receiver for receiving said sets of transmitted signals,*
   *implanted means for verifying that the received signals in each set are accurate and for producing an accurate signal when each signal in a set has substantially*

*either a first waveform or a second waveform, said means for verifying comprising*

*a second external means for transmitting said generated set of signals,*

*a second implanted receiver for receiving said second set of signals transmitted by said second means for transmitting, and*

*means for comparing the set of signals received by said implanted receiver with the set of signals received by said second implanted receiver and producing said accurate signal if they are identical*[.],

*an implanted memory address means for storing the memory address which is represented by the memory address representing signal in the set;*

*implanted means responsive to said accurate signal for entering selected ones of the received control signals in each set in the memory means at the memory address stored in said memory address means, and*

*implanted means for controlling said implanted stimulating signal generator with control signals from said memory.*

10. A programmable human tissue stimulator system comprising:

an implanted stimulating signal generator for generating body tissue stimulating pulses responsive to control signals, an implanted memory means for storing control signals for controlling said stimulating signal generator, external control means for generating a plurality of sets of signals, each set including control signals *and signals which represent a memory address in said memory means,* external means for transmitting said generated sets of signals, an implanted receiver for receiving said sets of transmitted signals, implanted means for verifying that the received signals in each set are accurate and for producing an accurate signal when each signal in a set has substantially either a first waveform or a second waveform, implanted *entering* means responsive to said accurate signal for entering selected ones of the received control signals in each set in a location in said memory means which is defined by [other] *the memory address representing* signals in the set, *said entering means including an implanted temporary storage means for storing the memory address in response to the generation of said accurate signal, said memory address stored in said temporary storage means thereafter defining the location in said memory means whereat said control signals are entered,* implanted means for controlling said implanted stimulating [signals] *signal* generator with control signals from said memory, each set of signals comprises a word comprised by binary pulses, each binary pulse rising from a leading edge to a first predetermined amplitude which extends first for a predetermined interval thereafter, then said binary pulse extends for a second predetermined interval at an amplitude level determined by its binary value, and thereafter extends for a third predetermined interval at a second predetermined value, means for determining that each signal has an acceptable waveform *that* includes[,]*:* first means responsive to the leading edge of a binary pulse for generating a reset pulse responsive to a binary value amplitude level change during said second predetermined interval, and second means responsive to the leading edge of a binary pulse for generating a reset pulse responsive to a change in said first predetermined amplitude during said first predetermined interval, register means into which a received binary word is transferred from said implanted receiver, and means for applying said reset signals to said register means to clear said register means.

11. A programmable human tissue stimulator system comprising:

an implanted stimulating signal generator for generating, responsive to control signals, body tissue stimulating pulse trains having parameters which are determined by said control signals, an implanted memory means for storing, at different locations, different parameter determining control words for determining the parameters of the pulse train output of said stimulating pulse signal generator, external control means for generating digital word signals, each word including a first plurality of binary bits representing a parameter for a pulse train, a second plurality of binary bits representing the storage location of said parameter in memory, and a third plurality of binary bits representing patient identifying data, an external transmitter for transmitting said digital word signals, an implanted receiver for receiving said transmitted signals,

[an] *first* implanted temporary storage means for storing word signals received by said receiver, means for verifying that [the waveform of] the received binary bits in a word have a predetermined acceptable waveform and clearing said *first* temporary storage if the waveform is not acceptable, implanted means for storing patient identifying data, means for comparing the received patient identifying data with stored patient identifying data and producing an acceptance signal if they are the same,

*transfer* means responsive to said acceptance signal for transferring said first plurality of binary bits [,] from said *first* temporary storage into the location in *said* memory means indicated by said second plurality of binary bits, [and] *said transfer means including second temporary storage means for storing said second plurality of binary bits in response to said accurate signal, said second plurality of binary bits in said second temporary storage means indicating the location in said memory means into which said first plurality of binary bits are transferred,* means responsive to said acceptance signal for clearing said *first* temporary storage.

14. A programmable human tissue stimulator system [as recited in claim 11 wherein there is included] *comprising:*

*an implanted stimulating signal generator for generating, responsive to control signals, body tissue stimulating pulse trains having parameters which are determined by said control signals,*

*an implanted memory means for storing, at different locations, different parameter determining control* words for determining the parameters of the pulse train output of said stimulating pulse signal generator, external control means for generating digital word signals, each word including a first plurality of binary bits representing a parameter for a pulse train, a second plurality of binary bits representing the storage location of said parameter in memory, and a third plurality of binary bits representing patient identifying data, an external transmitter for transmitting said digital word signals, an implanted receiver for receiving said transmitted signals, an implanted temporary storage means for storing word signals received by said receiver, a second external transmitter means for transmitting said generated word signals, a second implanted receiver for receiving the signals transmitted by said second external transmitter means, [and]

means for comparing the first and second pluralities of binary bits received by said second implanted receiver, with the first and second pluralities of binary bits in said temporary storage and producing a temporary storage clear signal when they are not alike, implanted means for storing patient identifying data, means for comparing the received patient identifying data with stored patient identifying data and producing an acceptance signal if they are the same, means responsive to said acceptance signal for transferring said first plurality of binary bits, from said temporary storage into the location in said memory means indicated by said second plurality of binary bits, and means responsive to said acceptance signal for clearing said temporary storage.

15. A programmable human tissue stimulator system as recited in claim 14 wherein said second external means for transmitting is a modulated light source, and said second implanted receiver is a light to electrical signal transducer.

21. A programmable human tissue stimulator system as recited in claim [4] *11* wherein said external control means includes:

means for generating a first signal for turning off and a second signal for turning on said implanted stimulating signal generator, and implanted switch means for applying operating potential to said implanted stimulating signal generator responsive to said first signal and for discontinuing the application of said operating potential responsive to said second signal.

*36. A programmable human tissue stimulator system comprising:*

*an implanted stimulating signal generator for generating, responsive to control signals, body tissue stimulating pulse trains having parameters which are determined by said control signals,*

*an implanted memory means for storing, at different locations, different parameter determining control words for determining the parameters of the pulse train output of said stimulating pulse signal generator,*

*external control means for generating digital word signals, including a first plurality of binary bits representing first identifying data, and a second plurality of binary bits representing a memory address in said memory means,*

*an external transmitter for transmitting said digital word signals,*

*an implanted receiver for receiving said transmitted digital word signals,*

*implanted means for storing a third plurality of binary bits representing second identifying data,*

*means for comparing the received first identifying data with the stored second identifying data, and for generating an acceptance signal when the comparison between the first and second identifying data indicates a prescribed correspondence therebetween,*

*an implanted temporary storage means for storing the second plurality of binary bits representing said memory address in response to the generation of said acceptance signal,*

*an implanted transmitter,*

*means for selectively connecting said implanted transmitter to said implanted memory means to selectively transmit the contents of the memory means at the memory address specified by the second plurality of binary bits stored in said temporary storage means.*

*37. A system for obtaining electrical biophysical signals from a plurality of implanted electrodes placed at a plurality of different tissue locations within a living body comprising:*

*a controller external to said living body having means for generating digital word signals specifying a selected tissue location from which it is desired to obtain electrical biophysical signals,*

*a transmitter within said external controller for transmitting said digital word signals,*

*an implanted tissue stimulator having said plurality of implanted electrodes connected thereto,*

*a receiver within said implanted tissue stimulator for receiving said digital word signals,*

*a transmitter within said implanted tissue stimulator for transmitting electrical biophysical signals received from one of said plurality of implanted electrodes,*

*switch means within said implanted tissue stimulator responsive to said digital word signals for selectively connecting to said transmitter a selected electrode placed at the selected tissue location from among said plurality of electrodes placed at different tissue locations within said living body, said selected electrode and location being specified by said digital word signal, whereby said transmitter will transmit electrical biophysical signals from said selected tissue location until said switch means responds to a different digital word signal and connects a different electrode to said transmitter, and*

*receiver means within said external controller for receiving said transmitted electrical biophysical signals.*

* * * * *